(12) United States Patent
Makrigiorgos

(10) Patent No.: US 7,033,757 B2
(45) Date of Patent: Apr. 25, 2006

(54) MUTATION SCANNING ARRAY, AND METHODS OF USE THEREOF

(75) Inventor: Gerassimos M. Makrigiorgos, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 09/858,200

(22) Filed: May 15, 2001

(65) Prior Publication Data

US 2002/0155451 A1 Oct. 24, 2002

Related U.S. Application Data

(63) Continuation of application No. PCT/US99/31177, filed on Dec. 29, 1999.

(60) Provisional application No. 60/114,196, filed on Dec. 30, 1998.

(51) Int. Cl.
*C12Q 1/68* (2006.01)

(52) U.S. Cl. .................. 435/6; 435/91.2; 435/287.2
(58) Field of Classification Search .............. 435/6, 435/287.2, 91.1
See application file for complete search history.

(56) References Cited

U.S. PATENT DOCUMENTS

| | | | | |
|---|---|---|---|---|
| 5,266,459 A | * | 11/1993 | Beutler | 435/6 |
| 5,376,526 A | * | 12/1994 | Brown et al. | 435/6 |
| 5,418,149 A | | 5/1995 | Gelfand et al. | |
| 5,459,039 A | | 10/1995 | Modrich et al. | |
| 5,736,330 A | | 4/1998 | Fulton | |
| 5,750,335 A | * | 5/1998 | Gifford | 435/6 |
| 6,174,680 B1 | * | 1/2001 | Makrigiorgos | 435/6 |

FOREIGN PATENT DOCUMENTS

| | | |
|---|---|---|
| WO | WO 93/22462 A1 | 11/1993 |
| WO | WO 98/30883 | 7/1998 |
| WO | WO 99/42622 A1 | 8/1999 |

OTHER PUBLICATIONS

Chee et al. Science, vol. 274, Oct. 25, 1996, pp. 610-614.*
Myers et al., *Methods in Enzymology*, 155:501-527 (1987).
Borresen et al., *Proc. Nat. Acad. Sci. USA*, 88:8405-8409 (1991).
Orita et al., *Proc. Nat. Acad. Sci. USA*, 86:2766-2770 (1989).
Nagamine et al., *Am. J. Hum., Genet.*, 45:337-339 (1989).
Roest et al., *Hum. Molec. Genet.*, 2:1719-1721 (1993).
Zafiropoulos et al., *Biotechniques*, 23:1104-1109 (1997).
Lewis et al., *Biotechniques*, 24:102-110 (1998).
Cotton et al., *Proc. Natl. Acad. Sci., USA*, 85:4397-4401 (1988).
Nelson et al., *Nature Genetics*, 4:11-18 (1993).
Nollau et al., *Clinical Chemistry*, 43:1114-1128 (1997).
Wodicka, *Nature Biotechnology*, 15:1359-1367 (1997).
Lockhart, D.J., *Nature Biotechnology*, 14:1675-1680 (1996).
Schena, M., *Trends Biotennol.*, 16:301-306 (1998).
Yang, T.T., *Biotechniques*, 18:498-503 (1995).
Ginot, F., *Human Mutation*, 10:1-10 (1997).
Wang, D.G., *Science*, 280:1077-1082 (1998).
Sidransky, D., *Science*, 278:1054-1058 (1997).
Hacia, J.G. et al., *Genome Research*, 8:1245-1258 (1998).
Lipshutz, R.J. et al., *Biotechniques*, 19(3):442-448 (1995).
Zimmerman et al., *Nucleic Acids Research*, 22(3):492-497 (1994).

(Continued)

*Primary Examiner*—Juliet C. Switzer
(74) *Attorney, Agent, or Firm*—Nixon Peabody LLP

(57) ABSTRACT

The present method is directed to using a mutation scanning array to identify mismatches or polymorphisms in multiple genes or the same gene in multiple individuals. The array can be a chip or a microsphere. Preferably, the array has elements containing immobilized oligonucleotides that collectively span at least 10 different whole genes.

12 Claims, 16 Drawing Sheets

OTHER PUBLICATIONS

Boturyn et al., *Tetrahedron*, 53(15):5485-5492 (1997).
Asaeda, A. et al., *Analytica Chimica Acta.*, 365:35-41 (1998).
Makrigiorgos, G.M. et al., *Int. J. Radiat. Biol.* 74(1):99-109 (1998).
Der, Sandy D. et al., Proc. Natl. Acad. Sci. USA, vol. 95 (No. 26), p. 15623-28, (1998).
McAllister, Linda et al., Genomics, vol. 47 (No. 1), p. 7-11, (1998).
Nelson, Stanley F., Electrophoresis, vol. 16 (No. 2), p. 279-285, (1995).
Cheung, Vivian G. et al., Nature Genetics, 18:225-230, (Mar. 18, 1998).

* cited by examiner

TECHNOLOGY FOR ISOLATING AND IDENTIFYING MUTATIONS
OVER HUNDREDS OR THOUSANDS OF GENES SIMULTANEOUSLY:
AN EXAMPLE OF SCREENING FOR A-TO-C TRANSVERSIONS.

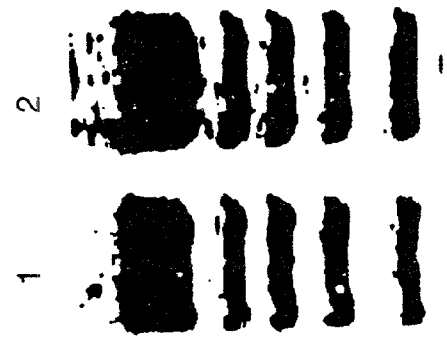
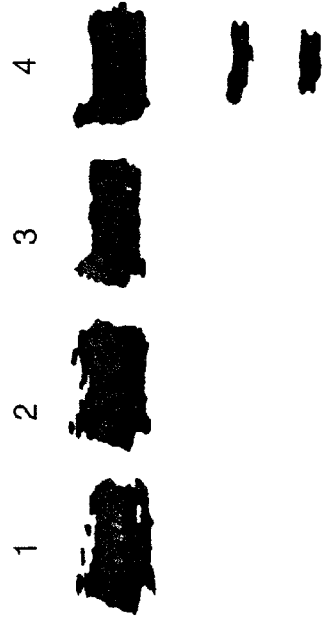
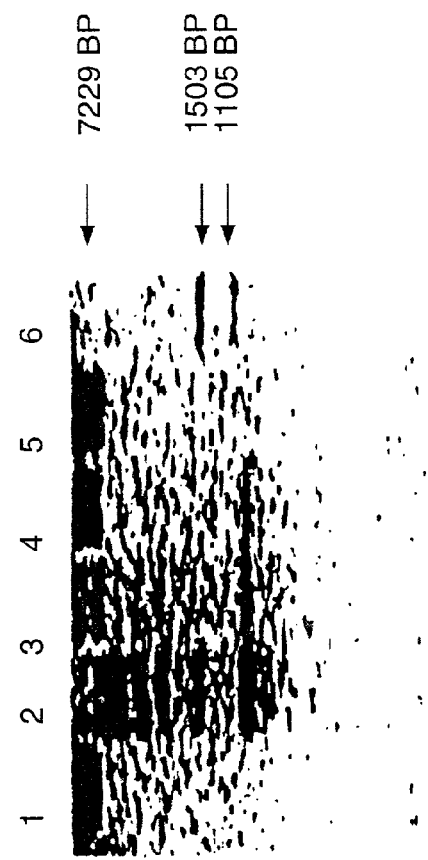
FIG. 5A
FIG. 5B
FIG. 5C

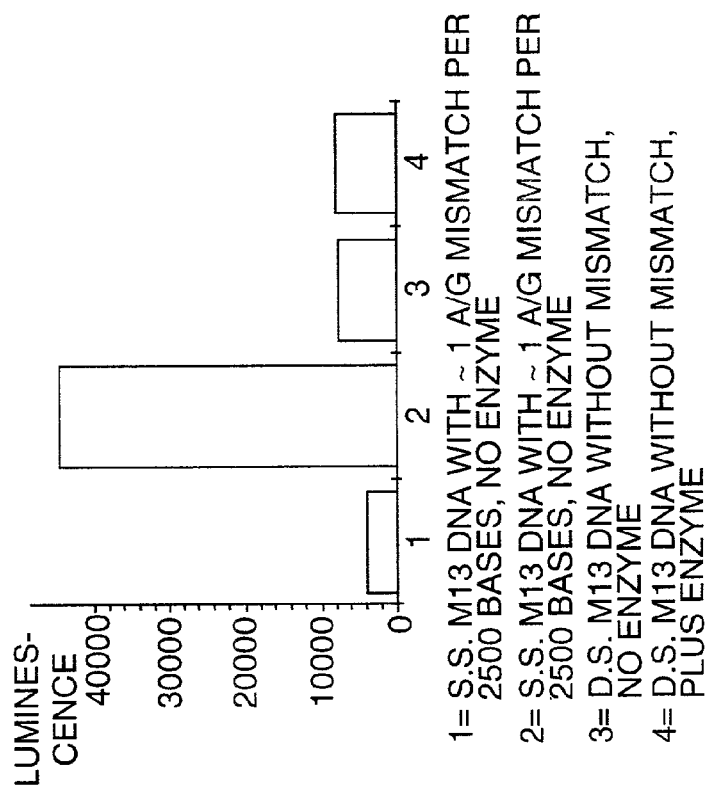

FIG. 8A

DETECTION OF MISMATCHES FORMED BY HYBRIDIZING OLIGONUCLEOTIDES WITH M13 DNA AND EXPOSED TO MutY ENZYME

1 = S.S. M13 DNA WITH ~1 A/G MISMATCH PER 2500 BASES, NO ENZYME
2 = S.S. M13 DNA WITH ~1 A/G MISMATCH PER 2500 BASES, NO ENZYME
3 = D.S. M13 DNA WITHOUT MISMATCH, NO ENZYME
4 = D.S. M13 DNA WITHOUT MISMATCH, PLUS ENZYME

FIG. 8B

1 = SINGLE STRANDED (S.S.) M13 WITH 1 A/G MISMATCH PER 2500 BASES, NO ENZYME
2 = S.S. M13 WITH 1 A/G MISMATCH PER 2500 BASES, PLUS ENZYME
3 = S.S. M13 WITH 1 A/G MISMATCH PER 2500 BASES, NO ENZYME
4 = DOUBLE STRANDED M13 WITHOUT MISMATCH, NO ENZYME
5 = D.S. M13 WITHOUT MISMATCH, PLUS ENZYME

M13mp19 DNA TESTED.
A = DNA ALONE
B = DNA PLUS MUTY
C = DNA PLUS 5mM METHOXYAMINE PLUS MUTY
D = DNA PLUS 5mM AED PLUS MUTY
E = DNA PLUS 10mM AED PLUS MUTY
F = DNA PLUS 5mM BARP PLUS MUTY

SIMPLIFIED PROTOCOL TO DETECT SNPs
AND MUTATIONS ON DNA CHIPS.

SEQUENCE LISTING

<160> NUMBER OF SEQ ID NOS: 3

<210> SEQ ID NO 1
<211> LENGTH: 49
<212> TYPE: DNA
<213> ORGANISM: Xenopus sp.

<400> SEQUENCE: 1
gtctcccatc caagtactaa ccaggcccga ccctgcttgg cttccgatt          49

```
<210> SEQ ID NO 2
<211> LENGTH: 49
<212> TYPE: DNA
<213> ORGANISM: Xenopus sp.

<400> SEQUENCE: 2
aatcggaagc caagcagggt agggcctggt tagtacttgg atgggagac                49

<210> SEQ ID NO 3
<211> LENGTH: 49
<212> TYPE: DNA
<213> ORGANISM: Xenopus sp.

<400> SEQUENCE: 3
aatcggaagc caagcagggt agggcctggg tagtacttgg atgggagac                49
```

MUTATION SCANNING ARRAY, AND METHODS OF USE THEREOF

CROSS-REFERENCE TO RELATED APPLICATIONS

This application is a continuation under 35 U.S.C. § 120 of International Application No. PCT/US99/31177, filed Dec. 29, 1999, which designated the U.S. and claimed the benefit under 35 U.S.C. § 119(e) of U.S. Provisional Application No. 60/114,196, filed Dec. 30, 1998.

STATEMENT AS TO FEDERALLY SPONSORED RESEARCH

This invention was made with Government support under grants R29 CA63334, K04 CA69296, and RO1 CA72046, awarded by the USPHS. The Government may have certain rights in the invention.

FIELD OF THE INVENTION

The present invention is directed to mutation scanning arrays, and methods of use thereof. In a preferred embodiment the method can be used to rapidly identify mutations and/or polymorphisms on a nucleic acid segment, or in an arbitrary mixture of nucleic acid segments or genes.

BACKGROUND OF THE INVENTION

The detection of mutations has been an area of great interest in recent years. For example, mutations in certain genes have been associated with a variety of disorders—ranging from blood disorders to cancers. Genetic tests are thus becoming an increasingly important facet of medical care. Consequently, there has been an emphasis on the ability to rapidly and efficiently detect mutations and polymorphisms.

Many electrophoretic techniques have been developed to rapidly screen DNAs for sequence differences by which such mutations can be detected. Denaturing Gradient Get Electrophoresis (DGGE) [Myers, R. M., Maniaris, T. and Lerman, L., *Methods in Enzymology*, 155, 501–527 (1987)], Constant Denaturant Gel Electrophoresis (CDGE) [Borresen, A. L., et al., *Proc. Nat. Acad. Sci. USA*, 88, 8405 (1991)], Single Strand Conformation Polymorphism (SSCP) [Orrita, M., et al., *Proc. Nat. Acad. Sci. USA*, 86, 2766–2770 (1989)], Heteroduplex Analysis (HA) [Nagamine, C. M., et al., *Am. J. Hum, Genet.*, 45,377–399 (19 ?9)] and Protein Truncation Test (PTT) [Roest, P. A. M., et al., Hum. Molec. Genet., 2,1719–1721 (1993)] are frequently used methods. Many labs use combinations of these methods to maximize mutation detection efficiency. All these methods require gel electrophoresis. Methods that do not require gel electrophoresis also exist. For example, selective hybridization on immobilized target sequences allows screening for rare known mutations [Zafiropoulos, A., et al., *Biotechniques* 223, 1104–1109 (1997)], while mass-spectrometry has been used to detect mutations by analyzing molecular weight of proteins [Lewis, J. K., et al., *Biotechniques* 24, 102–110 (1998)].

A fundamental problem with currently existing mutation and polymorphism detection methods is that they only screen for mutations on a single gene at a time (i.e. the method is directed to looking at a 'gene of interest', that is suspected of having a mutation). Given that the human genome has 50,000–100,000 genes, this is a severe limitation. It is likely that unknown mutations and polymorphisms in several other genes both known and unknown, exist simultaneously with mutations/polymorphisms in the 'gene of interest'. However, mutations in those other genes would likely not be identified. Therefore a method that can perform 'mutation/polymorphism scanning' in for a wide array of genes simultaneously, without the initial need for identifying the gene one is screening would be useful. Gel-electrophoresis-based methods are essentially restricted to examining mutations in a single gene at a time. Attempts have been made to devise non-gel electrophoretic methods to identify mutations, that would not be restricted to a single gene [Cotton et al., *Proc. Natl. Acad. Sci. USA* vol. 85, pp 4397–4401, (1988)] [Nelson, S. F. et al., *Nature Genetics*, 4, 11–8, (1993 May)] [Modrich, P., et al., Methods for Mapping Genetic Mutations. U.S. Pat. No. 5,459,039, (1995)]. These methods, however, have had limited success (Nollau P. and Wagener C., *Clinical Chemistry* 43:1114–1128 (1997)) since they are complicated, typically requiring several enzymatic steps and they result in a large number of false positives, i.e. they frequently score mutations and polymorphisms in normal DNA. It would be desirable to have a method that allows highly sensitive and specific identification and rapid purification of sites that contain mutation/polymorphism over large spans of the genome.

Although DNA arrays and methodologies that can simultaneously scan a large set of DNA fragments for gene expression (e.g. the 'repertoire' and amount of genes expressed in normal vs. cancer cells) are known [Wodicka L, *Nature Biotechnology* 15: 1359–1367 (1997); Lockhart, D J, *Nature Biotechnology* 14: 1675–1680 (1996); Schena, M., *Trends Biotecnnol* 16: 301–306, (1998); Yang, T. T., *Biotechniques* 18: 498–503, (1995)], the ability to scan a large set of random DNA fragments for unknown mutations is a much more demanding process on which the technology is lagging [Ginot F., *Human Mutation* 10: 1–10 (1997)]. Thus far DNA array-based methods to scan for polymorphisms (SNPs) and mutations has been restricted to specific genes [Lipshutz, R. J., *Biotechniques* 19: 442–447 (1995); Wang, D. G., *Science* 280: 1077–1082 (1998)]. Whereas detection of unknown mutations over several genes requires a selectivity and sensitivity not currently achievable by present arrays [Ginot F., *Human Mutation* 10: 1–10 (1997)]. For example, when it comes to unknown mutation detection, even a single gene with a coding sequence of the size of APC (8.5 kb) is difficult to screen in a single experiment, especially when an excess normal alleles is simultaneously present [Sidransky D., *Science* 278: 1054–1058 (1997)]. Thus, current arrays do not scan whole genes from the 5' to the 3' end, but selectively sample the gene. For example, expression arrays are biased to the 3' end. It would be desirable to have a methodology that could sample genes over larger portions of a gene and multiple genes. A method that permits identification of mismatches over large spans of the genome would also be desirable.

SUMMARY OF INVENTION

We have found a method that permits one to overcome resolutions and other limitations existing in current DNA chip technology and utilize the existing DNA chip technology for mutations scanning hundreds or thousands of genes simultaneously and identifying short (50–300 bases) DNA segments that contain mutations or polymorphisms. This method comprises first identifying a DNA segment containing mismatches. Those mismatches can either be single nucleotide polymorphisms (SNP) or mutations. Thereafter, one selects a DNA segment of from about 50–300 nucleotides containing a mismatch. Those DNA segments can be amplified by PCR and then screened on the DNA chip. Accordingly, instead of selecting a single gene at a time and examining whether it contains mutations, the present methodology first scans DNA to identify and isolate mismatch-containing and thereby mutation-containing DNA fragments (genotypic selection), and then determines which genes these DNA fragments belong to, by using available DNA arrays. Thus, the search for mutations is transformed to the easier task of searching for genes on a DNA array to identify where the mismatch occurs. Accordingly, DNA arrays currently used for multiplexed gene expression scanning [Wodicka L, *Nature Biotechnology* 15: 1359–1367 (1997); Lockhart, D J, *Nature Biotechnology* 14: 1675–1680 (1996).; Schena, M., *Trends Biotecnnol* 16: 301–306, (1998); Yang, T. T., *Biotechniques* 18: 498–503, (1995)] can be used directly or with minor modifications known to the artisan based upon this disclosure to scan for mutation.

Any method of identifying a DNA segment that contains a polymorphism and, thus, mutations and/or polymorphisms can be used. For example, one preferred method of identifying DNA fragments containing such mismatches involved the following steps; (a) isolating the nucleic acid, e.g., DNA, to be screened for mutations (referred to as the target DNA), adding PCR primers, and hybridizing it with control DNA, to create mismatches. These mismatches occur at the exact positions of mutations or polymorphisms; (b) removing any pre-existing, spontaneous aldehydes by, for example, treating the DNA with hydroxylamine; (c) using repair glycosylase enzymes (Mut Y and TDG) to convert the mismatches to reactive sites, namely, aldehyde-containing a basic sites (these enzymes recognize mismatches and will 'cut' the nucleic acid base, e.g., adenine at that site to create a reactive site); (d) using compounds (e.g. ligands) with functional groups that at one site can covalently bind to the reactive sites on the DNA, and that at a second site contain unique moieties that can be detected; (e) binding antibodies or avidin to the detectable second sites of the DNA-bound ligands. These antibodies or avidin may carry chemiluminescent or other indicators, so that the total reactive sites on the nucleic acid, e.g., DNA segment(s) tested is quantified, e.g. by chemiluminescence; (f) purifying the segments where a reactive site is present (e.g. by immunoprecipitation, or by ELISA-microplate-based techniques, or by microsphere-based techniques). The rest of the nucleic acid, e.g., DNA that does not contain mismatches can then be discarded; and (g) amplifying the remaining, mismatch containing nucleic acid, e.g., DNA, by PCR using the primers added in the first step. That mismatch-containing DNA can then be used in the above-described method with our mutation scanning arrays. (These arrays are sometimes also referred to as DNA chips.) Using the arrays of the present invention one can determine which gene each identified mismatch belongs to. Thereafter, known techniques can be used to determine whether that mismatch is a mutation that either causes the disorder or is associated with the disorder or simply an allelic variation, i.e. a polymorphism.

More specifically, the present invention permits biochemical approaches for chemically modifying mutations in a target nucleic acid sequence. The mutations are converted to mismatches following hybridization with control nucleic acid sequence. The mismatches in the hybrid nucleic acid, e.g. DNA can then be covalently bound by a ligand molecule, and then identified by a detectable moiety. Subsequently the mismatch-containing DNA can be purified by known means such as immunoprecipitation and the mutation-containing genes detected.

The target nucleic acid can be cDNA or genomic DNA. For example, the DNA can be any mixture containing one or various sizes of DNA, such as cDNA synthesized from the whole mRNA collected from cells that need to be screened for mutation/polymorphism; or fractions thereof; or the whole genomic DNA collected from cells that need to be screened for mutation/polymorphism; or fractions thereof; or any combination of the above digested into smaller pieces by enzymes. The use of cDNA is preferable.

This method can also be used to detect a variety of other labeled DNA sites such as DNA lesions that are converted to reactive sites by glycosylase enzymes or by chemical means (e.g. clustered DNA-damaged sites; a basic sites; carcinogen-DNA adducts; damaged DNA bases). In these embodiments, mixing of the target DNA with wild-type DNA to create mismatches is not needed. Enzymes will recognize damage and will generate reactive sites directly in the target DNA. Such enzymes include all known glycosylases, such as endonuclease III, uracil glycosylase, T4 endonuclease V, 3-methyladenine DNA glycosylase, 3- or 7-methylguanine DNA glycosylase, hydroxymethyluracile DNA glycosylase, FaPy-DNA glycosylase, M. Luteus UV-DNA glycosylase. Also, chemical agents such as bleomycin, alkylation agents or simple acid hydrolysis can generate reactive sites automatically in target DNA without any enzyme. The crucial step however is again the same, i.e. addition of some compound to the reactive site of a DNA lesion, which allows identification of the DNA-containing the lesion.

BRIEF DESCRIPTION OF THE FIGURES

FIG. 4A shows detection of AP sites in genomic calf thymus DNA depurinated for 15 seconds, without treatment (bar 1) or following treatment (bar 2) with hydroxylamine. FIG. 4B shows detection of spontaneously generated AP sites in hydroxylamine-treated genomic calf thymus DNA at pH=7.0, at a temperature of 37° C. (curve 1) or 4° C. (curve 2).

FIGS. 5A–5C shows gel electrophoresis of Mut Y-treated DNA, examined on denaturing gels. FIG. 5A shows 49-mer double stranded oligonucleotides that are Mut Y-treated and visualized on polyacrylamide gels following SYBR GOLD staining. Lane 1, no mismatch, no Mut Y. Lane 2, no mismatch, plus Mut Y. Lane 3, A/G mismatch, no Mut Y. Lane 4, A/G mismatch, plus Mut Y. FIG. 5B shows double standard homoduplex mixtures (DNA ladder, 27–500 base pairs) are Mut Y-treated and visualized on polyacrylamide gels following SYBR GOLD staining. Lane 1, no Mut Y. Lane 2, plus Mut Y. FIG. 5C shows single stranded M13 DNA (7,249 bases) are enzymatically-treated and visualized on agarose gels following ethidium staining. Lane 1, M13 DNA, no Mut Y. Lane 2, M13 DNA, plus Mut Y. Lanes 3–6, molecular weight markers.

FIGS. 8A and 8B show BARP-based chemiluminescence detection of Mut Y-treated DNA fragments of varying length: FIG. 8A shows chemiluminescence from single stranded M13 DNA (that forms ~3 mismatches over 7249 bases) and double stranded homoduplex M13 DNA (no mismatches) enzymatically-treated by Mut Y, BARP-labeled and captured on microplates. Bar 1, s.s. M13 DNA, no Mut Y. Bar 2, s.s. M13 DNA, plus Mut Y. Bar 3, d.s. M13 DNA, no Mut Y. Bar 4, d.s. M13 DNA, plus Mut Y. FIG. 8B shows gel electrophoresis of the same DNA, and demonstrates that, in agreement with the chemiluminescence results in FIG. 8A, only single stranded M13 plus Mut Y demonstrate DNA digestion (see bands in Lane 2).

FIG. 9A shows chemiluminescence detection of a single mutation (A-to-C transversion) engineered in a p53 gene which is incorporated in a 7091 base pair plasmid. Plasmids containing the mutation were first digested into smaller DNA fragments (400–2,00 bp) by exposure to RSAI enzyme. These were then melted and hybridized with normal plasmids to form mismatches at the position of the mutation. The DNA was then enzymatically-treated with Mut Y to convert mismatches to aldehydes, BARP-labeled and captured on microplates. Bar 1, plasmid with mismatch, no Mut Y. Bar 2, plasmid with mismatch plus Mut Y. Bar 3, normal plasmid, no Mut Y. Bar 4, normal plasmid, plus Mut Y. FIG. 9B shows the variation of the chemiluminescence signal obtained when different amounts of mismatch-containing plasmid treated by Mut Y and BARP are applied on microplates.

FIG. 10A demonstrates the binding of the compound, AED, (2-(aminoacetylamino) ethylenediamine) to reactive sites generated at position of mismatches in DNA by the enzyme Mut Y. The figure shows samples of M13 DNA containing mismatches, treated with enzyme and various compounds, stained with ethidium bromide and examined via gel electrophoresis. A sample of M13 DNA without enzymatic treatment shows a single bright band in lane A. The sample of plasmid DNA treated with the enzyme Mut Y shows multiple bands, demonstrating the expected recognition and cutting of mismatched bases by Mut Y in lane B. Lane C In Lanes C, D and E, the Mut Y treatments are carried out in the presence of 5 mM methoxyamine (C) or in presence of the novel compound AED (D, 5 mM and E, 10 mM AED respectively). The disappearance of the bands in lanes C, D and E is an indication of covalent high labeling of DNA by methoxyamine or by AED, at the positions of reactive sites generated by Mut Y. In Lane F, the treatment of DNA was as in Lanes E and D, but another aldehyde reactive compound (BARP) was used instead of AED. Lane F still shows the same multiple bands as those generated in the absence of compound (see Lane B), indicating an inefficient labeling of aldehyde sites by BARP.

FIG. 10B demonstrates the superior DNA binding of AED over BARP or FARP when reactive sites are generated at position of mismatches in DNA by the enzyme TDG. Lanes 1 and 2, G/T mismatch-containing oligonucleotide, no enzyme. Lane 3, G/T oligonucleotide with TDG enzyme. Lane 4, G/T oligonucleotide with TDG enzyme in the presence of 5 mM methoxyamine. Lane 5, G/T oligonucleotide with TDG enzyme in the presence of 5 mM BARP. Lane 6, G/T oligonucleotide with TDG enzyme in the presence of 5 mM AED. Lane 7, G/T oligonucleotide with TDG enzyme in the presence of 0.5 mM FARP.

DETAILED DESCRIPTION OF THE INVENTION

Figure 1:
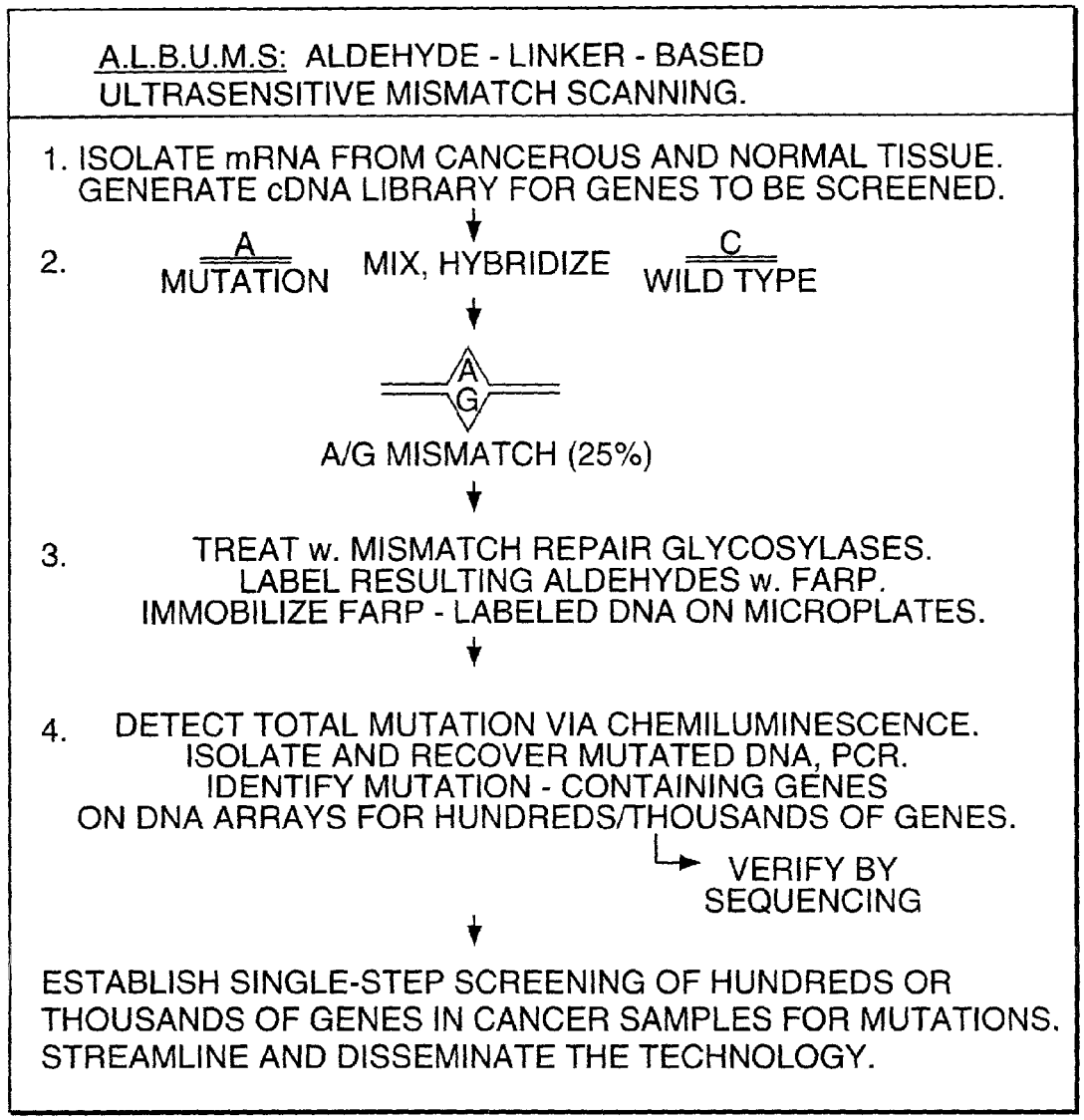
FIG. 1 shows a schematic of how the present technology is applied for identification of mutations in a complex mixture of genes, e.g. screening for C to A transversions over hundreds or thousands of genes simultaneously.

The present method permits biochemical approaches for chemically identifying the mismatch sites in, for example, the target DNA sequence. The target DNA can be identified by a detectable moiety and subsequently detected and purified by immunoprecipitation, microplates or microsphere technologies. Subsequently, the purified mutation-containing DNA fragments can be used in single-step screening of these mismatches by a wide variety of hybridization techniques (DNA chips, large-scale hybridization arrays, etc.)

For example, in trying to detect unknown mutations it has thus far proven difficult to screen for a single gene of about 8.5 kb (such as APC) in a single experiment, especially when an excess of normal alleles is simultaneously present [Sidransky, D. *Science* 278: 1054–1058 (1997)]. By contrast, the present method can screen multiple genes at once and/or multiple individual, and selects and isolates only those fragments containing a mutation/polymorphism. These mismatch-containing segments can be amplified by PCR and used, for example, in a DNA array to simply search for the matching gene in the array to identify which genes these mutation-containing fragments belong to. Consequently, existing arrays for multiplexed gene expression scanning such as known in the art can be used. For example, Affymetrix Hu6800 DNA Chip, or known arrays [Wodicka, L. et al, *Nature Biotechnology:* 15: 1359–1367 (1997); Lockart, D. J. et al, *Nature Biotechnology* 14: 1675–1680 (1996); Schena, M. *Trends Biotechical* 16:301–306 (1998): Yang, T. T. et al. *Biotechniques* 18: 498–503 (1995); Ginot F. *Human Mutation* 10: 1–10 (1997)].

In order to increase resolution (i.e. definition of the gene segment containing the mutation/polymorphism) the fragment should be smaller. However, in order to effectively prepare large amounts of mismatch-containing fragments by standard techniques such as PCR, the fragments should be at least about 50 bases. In some instances for ease of operation, a loss in resolution can be tolerated and larger fragments used.

Preferably the mismatch-containing fragment is 50–300 bases, more preferably 50–200 bases, still more preferably 50–100 bases and most preferably about 50 bases.

The nucleotides on the array (gene elements) should be between 8–300 bases preferably no larger than the size of the DNA of the mismatch-containing fragments. For improved resolution, smaller sizes should be used. For example, 50 bases or less, more preferably 8–25 bases. Many arrays presently available use nucleotide fragments of about 25 bases. Typically, these nucleotide segments are selected to be close to the 3' portion of the transcript.

However, other DNA arrays as discussed, infra, can also be used. Such arrays, which contain fragments that span the whole length of the gene (i.e. from both the 5' end of the gene as well as the 3' end) are preferred.

These mutation scanning arrays can be used with any method that permits one to tag a DNA or mRNA mismatch, thereby permitting the rapid identification of mutations in nucleic acids, e.g. DNA, mRNA or DNA segment(s). One preferred method of identifying DNA-containing mismatches is disclosed in copending application U.S. Ser. No. (09/224,227). That method comprises (a) isolating the nucleic acid, e.g., DNA, to be screened for mutations (referred to as the target DNA), and hybridizing it with control DNA, to create mismatches. These mismatches occur at the exact positions of mutations or polymorphisms; (b) removing any pre-existing, spontaneous aldehydes by, for example, treating the DNA with hydroxylamine; (c) using repair glycosylase enzymes to convert the mismatches to reactive sites, namely, aldehyde-containing a basic sites (these enzymes recognize mismatches and will 'cut' the nucleic acid base, e.g., adenine at that site to create a reactive site); (d) using compounds (e.g. ligands) with functional groups that at one site can covalently bind to the reactive sites on the DNA, and that at a second site contain unique moieties that can be detected; (e) binding antibodies or avidin to the detectable second sites of the DNA-bound ligands. These antibodies or avidin may carry chemiluminescent or other indicators, so that the total reactive sites on the nucleic acid, e.g., DNA segment(s) tested is quantified, e.g. by chemiluminescence; (f) purifying the segments where a reactive site is present (e.g. by immunoprecipitation, or by ELISA microplate-based techniques, or by microsphere-based techniques). The rest of the nucleic acid, e.g., DNA that does not contain mutations can then be discarded; and (g) amplifying the remaining, mutation-containing nucleic acid, e.g., DNA, by PCR. That DNA can then be used with our DNA arrays in order to find which gene each identified mismatch belongs to. Thereafter, by known techniques determining whether that mismatch is a mutation that either causes the disorder or is associated with the disorder or simply an allelic variation, i.e. a polymorphism.

The present method will recognize mismatches formed upon hybridization of the target DNA and the control (wild-type) DNA. Those skilled in the art are aware that mismatches may appear as a result of inherited or acquired genetic alterations. Also, that not every mismatch is the result of mutation but that some mismatches simply represent polymorphisms that occur naturally in populations. Both the inherited and the acquired genetic alterations in DNA will cause a mismatch.

Furthermore, those skilled in the art are aware that because all eukaryotic cells contain two copies of each chromosome, one paternal and one maternal, differences between the two alleles of each gene may also cause mismatches. In this case one gene copy (e.g. the paternal) will act as a control DNA and the second gene copy (the maternal) will act as the target DNA, and the mismatches will form upon hybridization of maternal and paternal DNA (i.e. simply by self-hybridization of DNA present in cells). These inherited differences can represent either polymorphisms or mutations.

There are a number of ways known in the art to distinguish whether a particular mismatch is an inherited polymorphism or mutation, or an acquired mutation.

One method that can be used to identify acquired mutations is to have the control DNA come from the same individual. For example, when screening a malignant cell the control DNA can be obtained from the corresponding non-malignant cell. By screening first the non-malignant cell alone and then the malignant cell (or a mixture of malignant and non-malignant cells) a comparison of detected mismatches in the two cases can be made. Differences that appear solely on the malignant cell and not on the normal cell comprise acquired mutations which may have lead to the malignancy.

When inherited (genetic) mutations/polymorphisms (i.e. where the alteration from the wild-type is present at birth and in every cell of the body) need to be identified, only normal cells need to be examined. As explained, inherited differences between the two alleles will cause mismatches upon self-hybridization. Detection of these mismatches will indicate the positions of inherited polymorphisms or mutations. Thereafter, one standard method to discriminate inherited polymorphisms from inherited mutations is to screen kindred and to determine whether or not the mismatch is present in normal kindred (i.e. a benign polymorphism) or only present in kindred showing a particular abnormality (i.e. a debilitating mutation).

The use of databases categorizing mutations and polymorphisms has also been increasingly popular. Thus, comparison of an identified genetic variation with those contained in a database can in many instances be used to determine whether the detected mismatch in DNA is due to a mutation or due to a polymorphism. One can also look at whether the mismatch causes truncation in the expressed protein.

Finally, another method that can be used to discriminate among mutations and polymorphisms is by the use of in-vivo assays. Thus, one can substitute a gene with at least one engineered base substitution mutation for the wild-type gene in an assay to determine whether or not the gene with the mutation can functionally replace a wild-type normal gene. If a gene can replace a wild-type normal gene in an assay and exhibit almost normal function that gene is not considered a mutation, but an allelic variation (i.e. polymorphism). If it cannot that gene will be considered a mutation.

One of the advantages of the present approach as opposed to mutation-detection methods presently being used is the ability to identify numerous mutations at diverse places in the genome. This permits one to determine if certain genes not presently associated with a particular abnormality may also have some relationship with that abnormality. For example, with hereditary non-polyposis colorectal cancer (HNPCC), mutations in the MSH2 and MLH1 genes are believed to be responsible for approximately 90% of the cases. A number of other genes have been identified as being responsible for the other 10% of the cases. However, in view of the cost of screening one typically looks primarily at MSH2 and MLH1. It may turn out when an array of genes are looked at the same time, that mutations in other genes also play a major role, in an individual with a particular condition. These other mutations may be associated with severity of the condition. By monitoring these additional genes and looking at disease state and recovery, one can develop a better idea of prognosis and treatment regimes than is currently available.

When using genomic DNA the skilled artisan is aware that numerous mismatches can and will occur in non-coding genetic regions. Looking at non-coding regions can permit the identification of mutations that affect expression and levels of expression. On the other hand when one is interested in looking for mutations in the expressed proteins it is preferable to use the mRNA to generate cDNA, and then form mismatches that can be detected by the present approach.

The preferred target nucleic acid is DNA, but mRNA can also be used. The DNA can be any mixture containing one or various sizes of DNA, such as cDNA synthesized from the whole mRNA collected from cells that need to be screened for mutation/polymorphism; or fractions thereof; or the whole genomic DNA collected from cells that need to be screened for mutation/polymorphism; or fractions thereof; or any combination of the above digested into smaller pieces by enzymes.

Thereafter, the DNA, mRNA, whole or smaller pieces thereof can be screened to identify those pieces containing a mismatch. The mismatch-containing pieces are then isolated from the remaining nucleic acid segments. As a result of this selection for mismatch-containing segments, it does not matter whether normal alleles outnumber aberrant segments. Moreover, one can use techniques such as PCR to amplify the mismatch-containing segments.

The control will be a wild-type fraction similar to the target. This wild-type likely will have no mutations. The control nucleic acid can be selected depending upon the intent of the test. For example, where acquired mutations in cancer cells are being screened, the control nucleic acid can come from a "normal" cell from the same individual. In other instances, for example, where an inherited (genetic) component may be involved the control DNA would come from a different subject than providing the nucleic acid; or simply differences among the paternal and maternal alleles can be examined by a self-hybridization of the DNA of the examined individual.

Following DNA isolation, the DNA is fragmented to reduce its size to the desired 50–300 base pairs, and generic PCR primers are added to the nucleic acids, in order to amplify the preparation at a later stage.

Thereafter in one embodiment, the target DNA is mixed and hybridized with wild-type DNA to create mismatches at the positions of differences, which are expected to be mutations/polymorphisms. One labels the mismatch and isolates the mismatch-containing DNA from the remaining DNA. In this manner one removes potentially interfering background signal. Thus, the only DNA being used with the DNA array is DNA that contains at least one mismatch.

Any method of labeling the mismatches in bulk can be used. One preferred method involves using repair glycosylases and specific aldehyde compounds to identify mismatches revealed by the glycosylases.

For example, creating a mixture of wild-type and target DNA and creating a mixture of segments containing the wild-type: wild-type, target DNA: target DNA and target DNA: wild-type pairs. The mixture is preferably treated with a compound such as hydroxylamine to remove any spontaneous aldehydes. Thereafter, the mismatches that occurred, which would be in the wild-type: target DNA hybrids, are recognized and converted to reactive sites (aldehydes) by enzymes such as a glycosylase repair enzyme such as Mut Y and thymine DNA glycosylases (TDG) (e.g., from Hela cells or E. colt). A unique feature of these enzymes is that they are highly specific, i.e. they act only on mismatches while they leave non-mismatch containing DNA completely intact.

These reactive sites are identified by using a compound containing an aldehyde-binding moiety such as —O—$NH_2$ (-hydroxylamine), or —$NHNH_2$ (-hydrazine) or —$NH_2$ (-amine) and also having a second moiety that reacts with a detectable entity (e.g. fluorescein, biotin, digoxigenin, which respectively react with antifluorescein antibody, avidin, and antidigoxigenin antibody. The antibodies may have chemiluminescence tags on them and thereby are detected). A unique feature of the present approach is that the aldehyde-binding moiety binds covalently to the enzyme-generated reactive sites. Combined with the specificity of the mismatch-repair enzymes, the use of covalently bound ligands to the position of mutations results in a sensitivity and specificity which is unparalleled by other methods for detection of mutations and polymorphisms.

The compounds have the general formula:

X-Z-Y, wherein X is a detectable moiety, preferably X is $NH_2$, SH, $NHNH_2$, a fluorescein derivative, a hydroxycoumarin derivative, a rhodamine derivative, a BODIPY derivative a digoxigenin derivative or a biotin derivative;

Y is $NHNH_2$, O—$NH_2$ or $NH_2$, preferably Y is $NH_2$,

Z is a hydrocarbon, alkylhydroxyl, alkylethoxy, alkylester, alkylether, alkylamide or alkylamine. Z may contain a cleavable group such as S—S. Z may be substituted or unsubstituted.

These reactive sites are identified by using a compound containing an aldehyde—binding moiety (Y) such as —O—$NH_2$ (-hydroxylamine), or —$NHNH_2$ (-hydrazine) or —$NH_2$ (-amine) and also having a second moiety (X) that reacts with a detectable entity (e.g. fluorescein, biotin, digoxigenin, which respectively react with antifluorescein antibody, avidin, and antidigoxigenin antibody. The antibodies may have chemiluminescence tags on them and thereby are detected). The aldehyde—binding moiety binds covalently to the enzyme-generated reactive sites. Combined with the specificity of the mismatch-repair enzymes, the use of covalently bound ligands to the position of mutations results in a high sensitivity and specificity.

One preferred embodiment of the invention has a general formula;

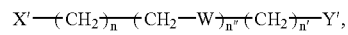

wherein X' is $NHNH_2$ or $NH_2$, preferably $NH_2$;

Y' is O—NH$_2$ or NH$_2$, preferably O—NH$_2$;

W is —NHC(O)—, —NHC(OH)—, —C(OH)—, —NH—, C—O—, —O—, —S—, —S—S—, —OC(O)—, or C(O)O—;

n is and integer from 0 to 12, preferably 4–7 and more preferably 6;

n' is an integer from 0 to 12, preferably 4–7, and more preferable 6, and n" is an integer from 1 to 4, preferably 1–2, and more preferably 1.

Preferably, the compound has a molecular weight between 100–500, more preferably 100–300, still more preferably 150–200.

Z and W can be substituted with groups that enhance the solubility of the resultant compound. Preferably the compounds of the formula X—(CH2)$_n$-(CH2-W)$_{n''}$—(CH2)$_{n'}$—Y are overall soluble in the solvent used A preferred embodiment has the formula;

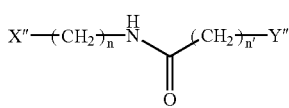

wherein X", Y", n, and n' are as described as above.

A more preferred compound is 2-(aminoacetylamino) ethylenediamine (AED), (NH$_2$CH$_2$CH$_2$NHC(O)CH$_2$ONH$_2$).

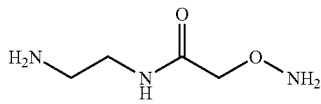

2-(aminoacetylamino) ethylenediamine (AED)

In another embodiment, the DNA reactive site recognized by enzymes such as glycosylases are identified by using compounds that contain a hydroxylamine reactive group. Examples of hydroxylamine compounds include FARP and FARPhc, both of which are fluorescent. FARP is a novel hydroxylamine containing derivative of fluorescein and FARPhc is a novel hydroxylamine containing derivative of hydroxy-coumarin.

These compounds have the general formula;

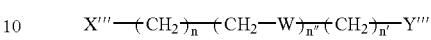

wherein Y''' is O—NH$_2$;

X''' is a fluorescent molecule, a fluorescein derivative or a hydroxy-coumarin derivative.

W, n, n', n"and n''' are defined as above.

More preferred compounds includes fluorescein aldehyde reactive probe, FARP, and fluorescent reactive probe hydroxycoumarin, FARPhc.

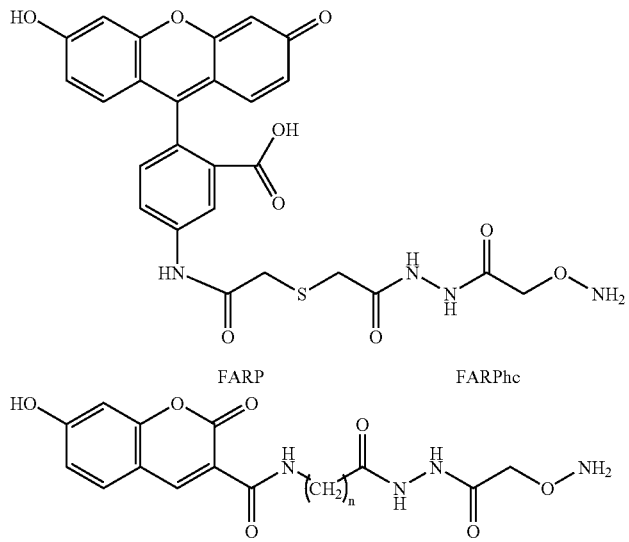

FARP          FARPhc

DNA samples containing mismatches that are prepared and treated with DNA-glycosylase enzymes as described above, will form covalent oxime bonds to FARP and FARPhc.

In an alternative embodiment, the DNA reactive sites recognized by enzymes such as glycosylases are identified by using compounds that contain a hydrazine reactive group. An example of this class of compounds includes biotin hydrazine. The present invention allows using hydrazine compounds to label reactive sites generated by the DNA-glycosylase enzymes. In yet still another alternative embodiment, the compound is a biotin aldehyde reactive probe, such as BARP, a biotinylated derivative of hydroxylamine [BARP, Kubo, K, et al., *Biochemistry* 31:3703–3708 (1992)].

These biotinylated hydroxylamine or hydrazine compounds have the general formula:

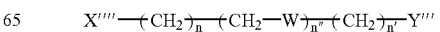

wherein Y''' is O—H₂ or NHNH₂;

X'''' is a detectable molecule, biotin or biotin derivative. W, n, n' and '' are defined as above.

For example, a Y moiety such as an amine should react with the aldehyde on for example the DNA, while the X group remains free for further modification and detection.

More preferred compounds includes biotin aldehyde reactive probe, BARP [Kubo, K., et al., *Biochemistry* 31:3703–3708 (1992)] and biotin hydrazide:

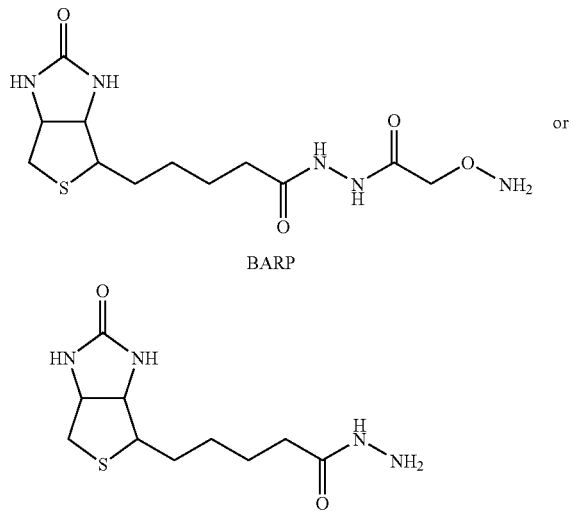

BARP

It was discovered that, following the recognition of mismatches by glycosylases such as Mut Y or TDG, and the resulting conversion to aldehyde-containing reactive sites, the enzyme has to be kept inactive, otherwise it interferes with the subsequent covalent binding of the ligand compounds. As a result, the conditions for reaction of hydroxylamines, hydrazines or amines with the enzymatically-generated aldehyde-containing reactive sites are at temperature of 4° C.–15° C. and at pH 6–7. (In the specific case of Y=NH₂ (amines), the presence of a reducing agent such as borohydride, 4° C.–15° C. for 1–3 hours is also required during binding to reactive sites). Following covalent attachment of the ligand compounds to reactive sites, the enzyme is then inactivated via heating at 70° C., for 10 minutes. Alternatively, to remove the enzyme a standard phenol-chloroform extract ion, or treatment with protein use K can be adopted.

When X=NH₂ (amine), in order for the covalently-bound ligand to be recognizable by an antibody, the free —NH₂ group is first covalently linked to an amine-binding compound with a recognizable group (e.g. a succinimidylester compound such as biotin-LC-succinimidyl ester; biotin-LC-SS-succinimidyl ester [Pierce]; fluorescein-succinimidyl ester; etc.). The reaction and purification conditions of such succinimidyl esters with —NH₂ containing compounds are well known.

When X—SH (sulfhydryl), in order for the covalently-bound ligand to be recognizable by an antibody, the free —SH group is first covalently linked to a sulfhydryl-binding compound with a recognizable group (e.g. a maleimide compound such as biotin-LC-maleimide; biotin-LC-SS-maleimide [Pierce]; fluorescein—aleimide; etc.). The reaction and purification conditions of such maleimides with -SH containing compounds are well known.

It was discovered that binding to reactive sites becomes much more efficient when small hydroxylamines (such as AED) are used. Therefore, the use of small compounds of the formula X'—(CH₂)n-(CH₂—W)n''-(CH₂)n'-Y, and of molecular weight less than 200 is preferred. These compounds are water soluble, can be incubated with DNA at a high molarity (e.g. 10 mM), and are able to diffuse fast enough to bind to reactive sites at a much higher level of efficiency than the other compounds (e.g. FARP, BARP) that have higher molecular weights and are less water soluble.

Purification of the mismatch-containing DNA preferably relies on the utilization of aldehydes as the recognition sites for mismatches resulting in covalent bonding of the marker molecule to these aldehydes. Therefore, the presence of contaminating nucleases that cleave DNA and create 3' hydroxyl groups—containing strand breaks (—a common problem in similar assays—) do not generate binding sites for the marker molecules. This method does not require the use of gel electrophoresis which compares DNA strand by their length or size. Thus, the generation of false positives from strand breaks generated by contaminating nucleases is thereby avoided. The method of the invention only detects labeled DNA following covalent binding of such aldehydes with ligand compounds and subsequent immobilization to a solid support, e.g., microplates. In addition, the length and diversity of DNA fragments are irrelevant to the assay, which is another advantage over gel-electrophoretic methods.

If borohydrite (sodium- or cyano-borohydrite) is present during the enzymatic lyase step, then a covalent cross-linking between enzyme and DNA occurs. In an alternative embodiment, one can introduce covalently-bound marker molecules (biotin, fluorescein, digoxigenin, or other fluorescent or chemiluminescent indicators) at the positions recognized by the enzymes.

To achieve this, the glycosylase enzymes are covalently labeled with an indicator molecule, either prior to DNA binding or after DNA binding and crosslinkage have taken place. For example using biotin as the indicator molecule, and Mut Y (trevigen) as the glycosylase enzyme the following procedure can be used.

To pre-label Mut Y with biotin, (i.e. Prior to DNA binding), the enzyme is incubated with a reactive analogue of biotin (e.g. Succinimidyl-ester of biotin, or biotin-lc-succinimidyl ester (Pierce), or biotin-maleimide, etc). Glycosylases are positively charged enzymes by virtue of the —NH₂-groups on their surface. These —NH₂— groups can be utilized for covalent crosslinking of the biotin indicator. The reaction of Mut Y with biotin-lc-succinimidyl ester takes place at ph 7.5–8.0, 1 h, 4° C. at a molar ratio of biotin:Mut Y of 5:1, or 2:1, or 1:1 (higher excess of biotin must be avoided if Mut Y is to retain its biological activity). Following that the unreacted biotin is removed by standard chromatography or by G25 filtration. The biotinylated Mut Y can now by used for enzymatic activity on a test DNA, to recognize, crosslink and label mismatches.

The assay is carried out as follows: first, DNA to be tested for mutations (test DNA) is mixed and cross-hybridized to DNA that contains no mutations (control DNA), in order to generate mismatches at the positions of mutations. Second, biotinylated Mut Y is added at a Mut Y:DNA molar ratio of 100:1, in the presence of 100 mM sodium borohydrite. Other reaction conditions and reaction buffers are standard, as recommended by the Mut Y supplier. Following crosslinkage of biotinylated Mut Y to DNA mismatches (a/g or a/c mismatches), the DNA is contacted by a streptavidin-coated solid support (e.g. Streptavidin-coated magnetic microspheres) in order to isolate DNA molecules containing biotinylated sites (i.e. Mutations). The isolated DNA can then be PCR-amplified and/or screened on appropriate mutation scanning arrays in order to identify the mutated genes. Alternatively, unmodified Mut Y can first be cross-linked to the DNA via borohydrite and then labeled with biotin through any of its available —$NH_2$— groups. Unreacted biotin is then removed from the DNA-enzyme mixture by known means such as by chromatography or G125 filtration. This alternate approach allows the enzyme to fully preserve its activity during the DNA binding process.

Other glycosylases that have lyase activity and can be crosslinked to DNA via borohydrite are known in the art and include: endonuclease III; endonuclease VIII; and hmu-DNA glycosylase.

Glycosylases that do not have lyase activity (e.g., Ap glycosylases: uracil glycosylase; thymine mismatch glycosylase; 3-ma-DNA glycosylase I or II; pd-DNA glycosylase; m-luteus uv glycosylase; etc) but only contain the base excision activity may also be adapted to function in the present invention. This is done by the subsequent use of endonuclease III glycosylase, following the initial base excision by the ap glycosylase. Enconuclease III recognizes the abasic site generated by the AP glycosylase and exersizes it lyase activity at that point. If borohydrite is present, endoIII is crosslinked at that position in DNA.

By following the above described approach, a biotin (or other indicator) can be introduced at the glycosylase-reactive sites in DNA (mismatches; mutations; polymorphisms; damaged bases; methylated bases; etc).

Once any of these compounds are covalently bound to the reactive sites, their reaction with a detectable group such as antibodies (e.g. avidin, antifluorescein etc.) and their subsequent detection (e.g. by chemiluminescence) and isolation (e.g. immunoprecipitation, avidin-coated microplates or microspheres, are well known in the art. For example, when X=$NH_2$, direct immobilization and purification of the mismatch-containing DNA is possible on microplates coated with activated succinimidyl ester [Costar] or maleic anhydrite [Pierce] which covalently bind the $NH_2$ group on the DNA-bound linker. When X=fluorescein, direct immobilization and isolation is achieved via antifluorescein-coated microplates [Boehringer]. And when X=biotin, direct immobilization and isolation is achieved via streptavidin-coated microplates (Pierce). In all cases, the immobilized DNA can be detected via alkaline-phosphatase or peroxidase-based chemiluminescence assays.

Those of ordinary skill in the art will recognize that a large variety of other possible detectable moieties can also be coupled to antibodies used to bind the DNA-coupled linkers at the positions of mismatches in this invention. Thereby providing additional methods to detect the antibody-bound mismatches on DNA. See, for example, "Conjugate Vaccines", *Contributions to Microbiology and Immunology*, J. M. Cruse and R. E. Lewis, Jr. (eds), Carger Press, New York, (1989).

The term "substituted," as used herein refers to single or multiple substitutions of a molecule with a moiety or moieties distinct from the core molecule. Substituents include, without limitation, halogens, hetero atoms, (i.e. 0, S and N), nitro moieties, alkyl (preferably $C_1$–$C_6$), amine moieties, nitrile moieties, hydroxy moieties, alkoxy moieties, phenoxy moieties, other aliphatic or aromatic moieties. Preferably the aliphatic or aromatic moieties are lower aliphatic or aromatic moieties, i.e. 12 or less carbons, more preferably 6 or less carbon atoms. Substituted compounds may be referred to as derivatives of the core structure.

Antibodies of the present invention can be detected by appropriate assays, such as the direct binding assay and by other conventional types of immunoassays. For example, a sandwich assay can be performed in which the receptor or fragment thereof is affixed to a solid phase. Incubation is maintained for a sufficient period of time to allow the antibody in the sample to bind to the immobilized labeled DNA on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized labeled DNA of the present invention is subsequently incubated with labeled antibody or antibody bound to a coupling agent such as biotin or avidin. Labels for antibodies are well-known in the art and include radionucleotides, enzymes (e.g. maleate dehydrogenase, horseradish peroxidase, glucose oxidase, catalase), fluorophores (fluorescein isothiocyanate, rhodamine, phycocyanin, fluorescamine), biotin, and the like. The labeled antibodies are incubated with the solid and the label bound to the solid phase is measured, the amount of the label detected serving as a measure of, for example, the amount of anti-FARP antibody present in the sample. These and other immunoassays can be easily performed by those of ordinary skill in the art.

The present method allows for extremely sensitive mismatch-scanning in diverse DNA fragments, thereby resulting in sensitive and high throughput mutation screening over several hundreds or thousands of genes at once. For example, it becomes possible for the screening and discovery of novel mutations in tumor samples which is instrumental to establish the pathogenesis of cancer and to establish new relations between mutations and cancer or other diseases. The new compounds and methods described above are also useful in analysis of the genetic background (polymorphisms, mutations) of any individual. High throughput genotyping and genotypic selection can be carried out by the present method.

Figure 13:
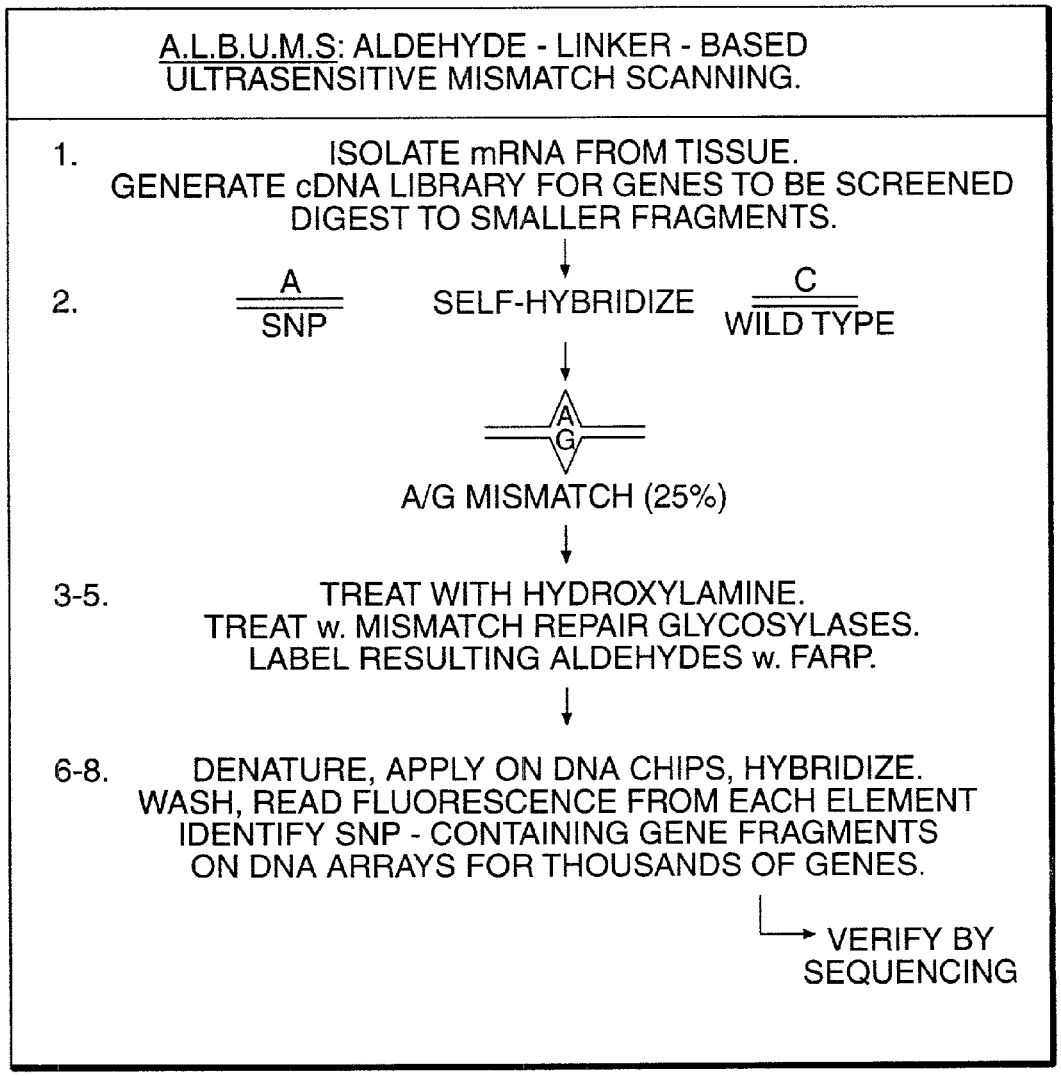
FIG. 13 is a procedure to detect polymorphisms and mutations.

In one embodiment for detecting SNPs or mutations is illustrated in the accompanying FIG. 13. In this embodiment, the following protocol can be used:

1. DNA to be screened (e.g. cDNA from an individual's lymphocytes) is digested to smaller fragments (50–300 base pairs) as detailed herein.
2. The digested fragments are self-hybridized to generate mismatches at positions of SNPs and mutations. Self hybridization can be carried out by heating (e.g., 2 minutes, 96° C.), then cooling to 65° C. for 1 hour. Alternatively, to avoid heating which may generate unwanted abasic sites, addition of formamide plus moderate heating (40–70° C.) can be used to perform the self hybridization.
3. Preferably, treatment with hydroxylamine follows, to remove unwanted abasic sites.
4. Treatment with mismatch repair glycosylases (Mut Y and TDG, separately or together) follows to convert mismatches to aldehydes.
5. Treatment with AED, FARP, BARP follows to label, e.g., fluoresceinate the generated aldehydes (corresponding to SNPs/mutations).
6. The sample is denatured, and directly applied to a DNA array, for example, DNA chips or beads where hybridization takes place.
7. Extensive washing follows, to remove unhybridized DNA or unbound FARP.

8. The label, e.g., fluorescence, from all elements on the DNA chip is read via appropriate devices (e.g. a scanning laser). These elements that display fluorescence correspond to gene fragments containing SNPs and mutations.

In the present method, one can use DNA arrays to identify the gene where the mismatch is present. For example, the Affymetrix, Inc. (San Diego, Calif.) HU6800 DNA chip, the Clontech Atlas™ DNA array (Palo Alto, Calif.); the Telechem International Array (San Jose, Calif.); the Genetix Ltd. array (Dorset, UK); and the BioRobotics Ltd. array (Cambridge, UK). The chip such as the Affymetrix DNA chip contains densely-packed DNA or RNA elements. For highest resolution the oligomers on the chip should be small. Preferably 8–50 nucleotides, more preferably 8–25 nucleotides. This will provide the highest resolution. However, the DNA or mRNA on the chips can be as large as the mismatch-containing DNA fragments, e.g. 50–300 nucleotides.

For example, using a conventional array, (e.g., the Affymetrix chip for detecting gene expression) the array will have multiple DNA or RNA elements densely packed, each comprising 25-mer oligonucleotides immobilized on a solid support. For each of the 6,800 genes which are represented on the chip, there are 20 elements each containing 25-mer oligonucleotides with a distinct portion of the mRNA sequence. Thereby the 20 elements 'sample' the mRNA sequence of the gene. In the current version, the immobilized probes are biased towards the 3' end of the mRNA, thus sequences towards the 5' end are not well represented. To use the array for detecting gene expression, users generate cDNA from the genes to be screened in the test sample (typically 1:g) and then perform in-vitro transcription to collect cRNA and biotinylate it(~50:g), 12 :g of which are hybridized on the chip (alternatively, cDNA can directly be applied on the chip without in-vitro transcription). If a gene is present in the test sample, then it hybridizes to an appropriate array element. Because the array is constructed to contain known gene sequences at known positions, all the transcribed genes are detected in a single step. The detection process utilizes addition of a marker-identifier such as a fluorescent scanner. The magnitude of the signal from each element signifies the degree of gene expression for the specific gene.

It should be noted that the present invention utilizes the same arrays but not anymore to detect gene expression (i.e. difference in signal among array elements), but mutations, which requires only detection of presence or absence of signal (indicating polymorphism/mutation in the specific gene fragment which was captured), thereby making the detection task much simpler.

Inherited single nucleotide polymorphisms (SNPs) and mutations can define a genetic predisposition towards several diseases, including cancer, cardiovascular, neurodegenerative and others. Indeed, acquired SNPs, mutations and loss of heterozygocity are particularly pertinent to cancer development, and early cancer detection. All of the above can be simultaneously detected in a single step by the above-described methodology.

Figure 11:
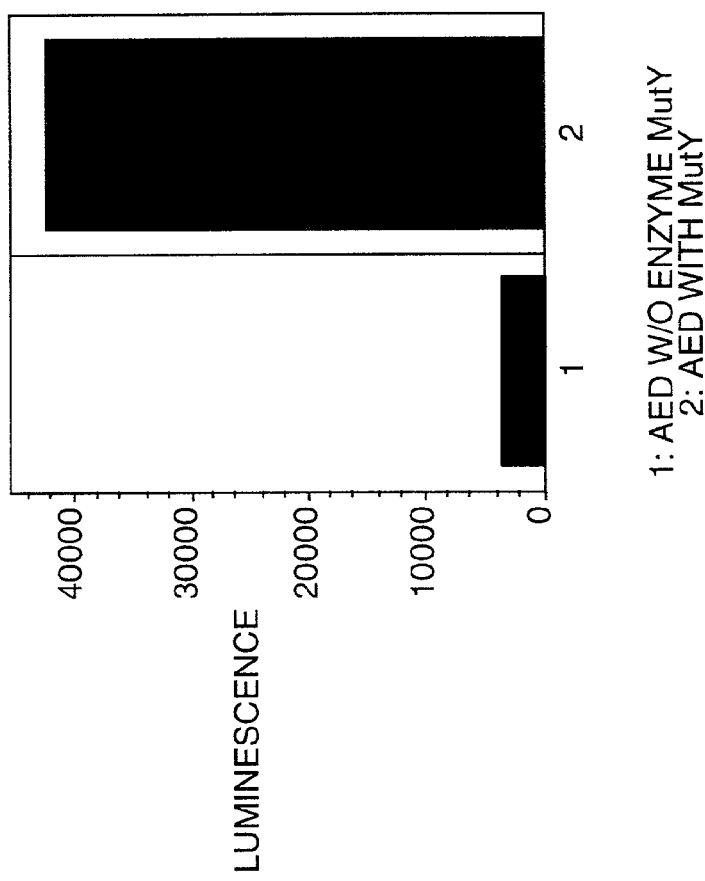
FIG. 11. AED-based chemiluminescence detection of mismatches obtained when mismatch-containing s.s. M13 DNA is Mut Y treated in the presence of 5 mM AED. Bar 1, M13 DNA without Mut Y enzyme. Bar 2, M13 DNA with Mut Y enzyme.

For example, cDNA for tumor and normal issue of a single individual is prepared. (See FIG. 11) Because inherited polymorphisms is a frequent event (average 1 SNP per 1000 bases), several genes will have more than one SNP. Also, the tumor genes will contain one or more inherited SNPs as well as occasional acquired SNPs/mutations. Next, the cDNA is digested by enzymes down to small fragments (~100–200 bp), thereby generating fragments that are likely to contain only one -or none-genetic alternations. Then, each sample is melted and self-hybridized, to generate mismatches at positions of SNPs/mutations. The above-described methodology using an X—Z—Y compound is applied as described above, to isolate only the mismatch-containing cDNA.

The mismatch-containing cDNA is PCR-amplified, labeled, e.g. biotinylated, and applied on a an array such as the Affymetrix chip: Each mismatch-containing fragment will hybridize to its complementary oligonucleotide on the array, thereby revealing which gene and which gene region (to within 100–200 base pairs) the SNP/mutation belongs to. By comparing arrays A and B, both the inherited and the acquired SNPs/mutations can be derived. Loss of heterozygocity may occur when an acquired SNP/mutation occurs in the same gene with an inherited SNP/mutation. Such genes can readily be identified by comparing A and B.

Current chip arrays, which are intended for gene expression detection, including the Affymetrix chips, utilize immobilized oligonucleotides which are biased toward the 3' end of mRNA. Accordingly, the 5' end of the gene is underrepresented. Moreover, present mutation detecting technology cannot adequately utilize existing chips. By contrast, our methodology makes it possible to identify mismatches over diverse sections of the genome using chip technology.

A preferred Mutation Scanning Array should contain immobilized oligonucleotides, preferably 8–25 bases long, which span the whole mRNA sequence of each gene represented on the array, and not biased toward one or the other mRNA end. Rather they should cover the whole genes being studied. In some preferred instances, one uses genomic DNA to make the array and would use both coding, and non-coding portions. As mentioned, the oligonucleotides can be larger, but by increasing size, resolution is lost. The oligonucleotides should sample the mRNA in intervals not bigger than the DNA fragments isolated by present method preferably 50–100 bases but capable of ranging from 50–300 bases. In this manner the mismatch-containing fragment will be assured of finding a complementary sequence on the array. When immobilized oligonucleotides on the array are arranged to sample the mRNA at small intervals (e.g. 20 bases) there will be redundancy of information upon hybridization of the mutant fragments to the DNA chip, as each fragment may simultaneously hybridize to two or more immobilized oligonucleotides. In this case, by using the combined information from all array elements, a better resolution of the position of the mutation will be achieved.

This Mutation Scanning Array can be constructed using the same technologies as for the current arrays. The above-described modification will allow SNPs/mutation detection over the whole length of the immobilized genes to be identified. The immobilized genes can be either the whole genomic cDNA library, or an arbitrary fraction of that, or a specific collection of genes that are known to be related to a specific disease (i.e. disease specific arrays).

A major advantage of the present mutation scanning chip technology is that it can detect SNPs/mutations in the presence of an excess of normal alleles in the initial sample because the methodology first isolates the mutants, and the array subsequently identified the gene. This is currently impossible to do with existing technology.

A preferred kit will comprise reagents to isolate mRNA from tissues, synthesize cDNA, fragment DNA to 100–200-mers and add PCR, form heteroduplexes, use Mut Y and TDG enzymes to cut the mismatches, remove spontaneous aldehydes, apply the X—Z—Y compounds e.g., FARP/BARP/AED, to detect mismatches, isolate mutant/polymorphic fragments by immobilization on microplates, recover and PCR mutants/polymorphisms, and finally apply on an array to detect SNPs/mutations at specific genomic positions.

The kit can be used to screen an individual for inherited susceptibility to cancer, cardiovascular disease, neurodegenerative disorders, etc. by mapping positions of heterozygocities and SNPs in the whole genome or in selected fractions of the genes.

The present methodology also permits one to detect early onset of cancer (acquired SNPs/mutations) from tissue biopsies or excretions. The present technology also permits research labs to detect new mutations and correlate them to other diseases.

The ligand compounds described demonstrated excellent detection of DNA mismatch-repair recognition sites. In addition, based on our discovery that small (MW<200–250) compound allow high binding efficiency (>50%) to DNA reactive sites, new compounds (like AED) were designed, synthesized and tested. These were shown to bind reactive sites generated by Mut Y much more efficient than compounds of higher (>250) molecular weight. Preferred compounds are small, water soluble, do not encounter significant steric interactions with DNA and can diffuse fast to the enzymatically-generated reactive sites on DNA. This class of new bifunctional compounds is also uniquely designed to retain their water solubility as the chain length is extended. The simultaneous addition of internal polar functional groups along with methylene groups maintains the water solubility of these compounds in spite of the increased length of the molecule. Care must be taken however to retain a low overall molecular weight for the final compound. Useful polar functional groups include; alcohols, esters, ethers, thioethers, amines and amides. This allows users of this method the flexibility to tailor the chain length of the compounds to suit their specific needs with out the loss of water solubility, which is essential.

In one method for obtaining DNA containing mismatches from a tumor sample, mRNA is isolated from a malignant cell. The corresponding mRNA from a healthy or normal tissue sample is also isolated. The mRNA from the normal tissue will serve as the wild-type control. A cDNA library can be made for each mRNA sample, the cancerous and wild-type. The two cDNA libraries are added together, for example in a 1:1 ratio and hybridized. (See FIG. 1) The hybridization produces a mixture of double stranded DNA. The double strands of DNA that consist of cDNA from the malignant cell hybridized with a strand of wild-type DNA will now typically contain some mismatches that are associated with the malignancy.

The mixture of hybridized cDNA is then treated with hydroxylamine to remove any spontaneous aldehydes, and then the hydroxylamine is removed via G25 filter centrifugation of the samples. The double stranded cDNA which is now void of pre-existing aldehydes, is then treated with a mismatch-repair glycosylase, such as Mut Y or TDG. Mut Y is a DNA-repair enzyme that recognizes mismatched adenosine nucleotides, and TDG recognizes mismatched thymines. Upon recognition, Mut Y or TDG remove the base by cleavage at the point of attachment to the deoxyribose sugar. Removal of the base by this method of cleavage results in the opening of the deoxyribose ring with formation of an aldehyde. Since pre-existing aldehydes were removed by hydroxylamine treatment, the only aldehydes are those generated at positions of mutations.

The resulting strands of cDNA now contain an aldehyde located at each point of mismatch. These resulting aldehydes are then treated with one of the compounds, e.g. the 2-(aminoacetylamino)ethylenediamine (AED) or one of its analogues, at low temperature so that further activity of the Mut Y/TDG enzymes is suppressed. The DNA labeled with AED is then selectively immobilized on microplates as described earlier in this text. The unlabeled DNA is then washed away leaving behind only AED labeled DNA attached to the microplate. The DNA with the labeled mutations, while immobilized on the microplates is then biotinylated and the mutations can be detected, for example, via chemiluminescence. Mutation-containing DNA can then be recovered from microplates for identification of the genes involved via PCR and large-scale hybridization techniques using the present mutation detecting arrays. Consequently, all mismatch containing genes are captured at once and the number of genes that can be simultaneously be screened is only limited by the total genes the DNA array created has to verify and identify the exact position of the mismatche(s) on each particular gene identified by the present invention, conventional procedures such as sequencing can be used.

This method can also be used to detect a variety of other DNA lesions that are converted to reactive sites by glycosylase enzymes or by chemical means (e.g. clustered DNA-damaged sites); abasic sites; carcinogen-DNA adducts; damaged DNA bases). In these embodiments, mixing of for example the target DNA with wild-type DNA to create mismatches is not needed. Enzymes will recognize damage and will generate reactive sites directly in the target DNA. Such enzymes include all known glycosylases, such as endonuclease III, T4 endonuclease V, 3-methyladenine DNA glycosylase, 3- or 7-methylguanine DNA glycosylase, hydroxymethyluracile DNA glycosylase, FaPy-DNA glycosylase, M. Luteus UV-DNA glycosylase. Also, chemical agents such as bleomycin, alkylation agents or simple acid hydrolysis can generate reactive sites automatically in target DNA without any enzyme. The crucial step however is again the same, i.e. covalent addition of compound to the reactive site of the DNA lesion, which allows subsequent sensitive detection.

The described technology can be used for mutation screening and for research. For example, the use of solid supports at every stage of the assay will substantially shorten the time required to screen tumor samples, improve its cost-effectiveness in terms of man-power as well as its reliability and reproducibility.

An alternative mutation scanning array to the chip array is the use of beads, sometimes referred to as microbeads or microspheres. For instance, magnetic microsphere technology can be utilized to immobilize heteroduplexes at an early stage of the assay. Following mRNA extraction from e.g., a host cell such as cancerous and normal samples, cDNA for e.g. 588 genes can be generated. Thereafter PCR primers that contain a cleavable (S—S) biotin are added. Hybridization of the cancerous cDNA with wild-type alleles generates heteroduplexes at the positions of base substitution mutations, and the DNA sample is immobilized on, for example, the streptavidin-coated magnetic microspheres (available from Dynal Inc.). From this point onwards, all subsequent steps of the ALBUMS assay can be conducted on the solid support.

The microspheres allow chemical/enzymatic treatment of the immobilized DNA and efficient, rapid separation of chemicals from DNA via magnetic immobilization of the microspheres during washing. For example, in one embodiment the assay uses hydroxylamine treatment to remove traces of aldehydes and subsequent complete removal of hydroxylamine via repeated (×3) ultracentrifugation through G25 filters. This can be time-consuming and result in an inevitable loss of sample, which can be important when tissue samples are limited. In contrast, by immobilizing the DNA magnetic microspheres, all subsequent steps become faster, easier and without DNA loss: Hydroxylamine treatment and removal, enzymatic treatment and washing, X—Z—Y treatment and washing, binding antifluorescein-AP to e.g. AED-trapped mismatches and washing, and finally chemiluminescent detection of mismatches are performed on the magnetic microsphere format.

Alternatively, to recover the DNA from magnetic microspheres and isolate the X—Z—Y, e.g. FARP, containing DNA, instead of adding antifluorescein-AP the immobilized DNA can be recovered by cleaving the disulfide (S—S) bond on the biotin by mild exposure to a reducing reagent (DTT, 50 mM, ~10 min, 25° C.).

To construct primers end-labeled with a cleavable moiety such as biotin, oligonucleotides containing a terminal aliphatic amine are ordered, and reacted with e.g. a biotin —S—S— succinimidyl ester (available from Pierce). Reactions of succinimidyl ester with amino-oligonucleotides and subsequent purification by reverse C18 column chromatography are standard procedures on which our group has had prior experience.

Following removal of DNA samples from the magnetic microspheres, the samples will be applied on e.g. antifluorescein-microplates to isolate e.g., FARP-containing heteroduplexes which subsequently will be recovered, PCR amplified and screened on the Clontech DNA hybridization array. Using the above procedures, base substitution mutations can be isolated via ALBUMS, amplified by PCR and screened on the DNA array in less than 24 hours. Thus, this technique results in a standardized procedure with easy access to researchers and clinicians for cost-effective, large-scale mutation screening of a target sample, such as cancer samples.

See also U.S. Pat. Nos. 5,736,330 and 5,981,180 and the products of Luminex Corporation (Austin, Tex.). Flow cytometry can be used for diverse applications in hematology, oncology, cell biology, etc. Apart from cultured cells, beads (also known as 'microbeads', 'microspheres') tagged with fluorescent probes, or with biomolecules carrying fluorescent probes, are commonly used. During flow cytometry, such fluorescent microbeads are forced to flow down a thin tube and are individually excited by one or more laser beams. Light emitted from each microbead is then individually filtered and measured by an attached light detector. Depending on the signals obtained, individual microbeads can be separated (sorted) from the rest of the microbead population. Common flow cytometers can collect individual light signals and sort 10,000–30,000 microbeads per second. As a result, $10^8$ microbeads can be sorted in less than one hour. Specialized flow cytometers can count individual microbeads at much higher rates. Multiparametric flow cytometry allows each individual microbead to be excited by several lasers at once, and illumination by each laser produces optical emissions at several discrete wavelengths and intensities, depending also on the type and amount of fluorescently-labeled biomolecules bound to the microbeads. As a result, passage of each individual microbead through the flow cytometer can result to emission of a large set (5–7) of signals, which are individually detected and stored on a computer. The capability of rapidly sorting individual microbeads depending on the collected parallel optical signals makes flow cytometry a powerful tool for analyzing numerous genes in a very short period.

When a microbead tagged with a specific gene, is also tagged with a combination of fluorescent probes it can be used in flow cytometry. The fluorescent probes with which the beads are tagged can have a variety of different fluorescent intensities. Consequently, for each bead there is a unique combination of intensities/fluorescent probes such that, passage of an individual bead through the flow cytometer uniquely identifies the immobilized gene. Further, if the gene immobilized on the bead has hybridized to a 'target DNA', the hybridization produces a unique fluorescent signal which may also be detected by the flow cytometer as the bead passes through. Therefore hybridization in hundreds or thousands of diverse genes can be rapidly detected, quantified and analyzed by this procedure.

Microbeads for flow cytometry are commercially available by several manufacturers (e.g. Polysciences; Molecular Probes). A typical microbead consists of an approximately spherical polystyrene 'core' with a diameter of 0.1–20 µm. The microbead can be tagged with indicator molecules such as fluorescent probes of appropriate wavelength, which are either directly bound to the microbead surface, or bound to a nucleic acid that coats the microbead surface, or fill the 'interior volume' of the microbead. When the microbead passes through the laser beam in a flow cytometer, an intense fluorescent signal is emitted, which is filtered and counted with a photomultiplier. Depending on constraints set by the user (e.g. certain intensity in the observed signal; or a certain combination of emitted fluorescent wavelengths) microbeads can be sorted into separate containers after passage through the cytometer laser beam.

Microbeads can readily be tagged with specific DNA fragments. A standard method to achieve this is to manufacture microbeads with 'functionalized surfaces', e.g. coated with carboxyl- or amino-groups, or with avidin, etc. Such microbeads are widely available. Binding of a nucleic acid on the functionalized surface is achieved via end-labeling the nucleic acid, which is then attached to the microbead surface. For example, if a primary amine is attached to the nucleic acid, then a carbodiimide-mediated reaction can attach the nucleic acid to the carboxyl-coated microbead. If a biotin is attached to the nucleic acid, then this will bind to the avidin-coated microbead, etc. The single stranded DNA attached to the microbeads will be called hereafter 'control DNA'.

When microbeads coated with control DNA are mixed and allowed to hybridize with single stranded 'target DNA' which is to be analyzed for gene expression, polymorphisms or mutations, hybridization will take place if a sequence complementary to the control DNA sequence exists. Hybridization should preferably be under conditions of at least moderate stringency, more preferably high stringency. These conditions can be obtained by varying salts, temperature, etc. and are well known in the art. See e.g., Sambrook, et al, *Molecular Cloning Second Edition*. The unhybridized DNA can then be removed from the solution, e.g. via centrifugation, if desired. (This is not an absolute requirement since flow cytometry will only count fluorescence bound to the microbeads and not in solution). Such hybridization of DNA in microbead-format is well known to those experienced in the art, (e.g. to isolate mRNA, poly-dT-coated microbeads are used). To detect signals from microbeads containing hybridized double stranded sequences the target DNA can be pre-labeled with a fluorescent probe. Accordingly, fluorescent signals from microbeads with control DNA hybridized to target DNA can be readily detected via flow cytometry.

In one embodiment, beads can also be labeled with a 'cocktail' of fluorescent probes, each fluorescent probe having a specific emission intensity (Such probes are often used for calibration purposes). Multiparametric flow cytometry, which is a common application, can simultaneously acquire signals from all fluorescent probes bound to the beads and measure their intensity.

For example, a flow cytometer can monitor simultaneously 6 fluorescent emission wavelengths (e.g. by using 3 excitation lasers with two different filters each). The bead can be labeled with, for example, fluorescent probes 1–5 chosen so that they have either distinct excitation or distinct emission wavelengths, with minimal overlap regions. Different amounts of each fluorescent probe can be incorporated on the bead, so that at least 20 distinct fluorescent intensities can result per probe (see, for example FIG. 14, where beads labeled with 5 different fluorescent intensities of fluorescein are depicted.

Accordingly, in this example there are up to 3,200,000 combinations of beads that can be constructed, each one different from the others, which upon passage through a flow cytometer would give a unique optical signature. (In practice one will not need to use so many combinations, as there are only about 70,000 human genes most of which may not need to be counted in a particular application. A typical application may utilize 1,000 human genes, represented by 1,000–20,000 different beads, each bead containing a different section of a gene).

If each bead is tagged with a different gene, or gene fragment, any desired number of genes can be analyzed in a single experiment, via flow cytometry. Assume also, that the 'target DNA' which is hybridized to the beads of known optical signature tagged with 'control DNA' is tagged with a 6th fluorescent probe, which gives a unique signal, clearly distinguishable from signals by probes 1–5. Upon passage through a multiparametric flow cytometer, each bead would yield (a) its optical signature by monitoring the intensity of emissions from probes 1–5, and thereby the identity of the control gene bound to the bead; and (b) the intensity of emission from probe 6 which would determine if, and to what extent the target DNA has hybridized to the control gene.

The flow cytometer used preferably has the ability to detect 'rare events'. Each B.U.S. will only rarely emit its unique optical signal since other beads will be counted most of the time. If 10,000 distinct B.U.S. are included in an aliquot, representing 1,000 human genes, the flow cytometer must be able to detect and discriminate 1 in 104 beads, without 'noise'. This is well within the capabilities of common flow cytometers, which can typically discriminate 1 in 105 events.

In some embodiments, enhanced software and computer storage space may be needed to record each event separately and store it in an appropriate 'bar histogram' (each bar representing a unique gene). Such software currently exists for applications that deal with a limited number of uniquely labeled beads/cells. The current invention requires that the software handles thousands of different parameters, following the optical detection of unique signatures from a total of 107 to 108 beads. Extension of the current software and disk storage space to satisfy the demands of the current application can readily be accomplished.

Several control genes and beads can be included in the flow-cytometric determination, in order to ensure that the method performs optimally.

The above method can be adapted for the detection of SNPs and mutations. In this approach, an intermediate step is used to isolate and purify only those DNA fragments that contain SNPs or mutations. This process can be carried out with the compounds and methodologies detailed herein.

Following isolation of those cDNA fragments (typically 50–200 base pair long fragments) that contain SNPs or mutations, the target DNA is hybridized to control DNA—containing B.U.S.-aliquots and processed via flow cytometry. The optical signature of those beads that present positive signals from probe 6 define the genes that contain SNPs and mutations in the population.

In order to detect SNPs and mutations, the control DNA which is attached to the beads has to be relatively short (e.g. in the region 10–100 base pairs) so that, following capture of a corresponding fragment that contains an SNP/mutation, the genomic region containing the genetic alteration is automatically defined with a good resolution (~100 base pairs). In addition, for each gene that will be examined, enough regions of the gene have to be immobilized (each region on a separate B.U.S.), so that the whole gene (from 3' to 5'-end) is adequately represented at regular intervals. In this manner, every target DNA fragment which is isolated and contains a genetic alteration will be assured of finding a complementary sequence to i hybridize in the B.U.S.-aliquot.

B.U.S. can be constructed with optimized properties and sold in a kit, for example, en masse manufacture by a commercial supplier. The kit can have reagents to attach multiple fluorophores and specific DNA sequences on a bead coated with streptavidin for use with biotin-end-labeled oligonucleotides for attachment to streptavidin-binding sites, as well as cocktails of amine-reactive fluorescent probes (e.g. succinimidyl esters of fluorescent probes) for the simultaneous attachment to the free primary amines of streptavidin. Alternatively, on carboxylic acid-coated beads, both the fluorescent compounds and amine-end-labeled nucleic acids can be attached.

The user can decide which and how many genes and which controls are included in each individual experiment, and can change the genes included 'at a moment's notice', in the next experiment. This is currently impossible with chip microarray technology. Furthermore the technique should be significantly cheaper than current chip microarray technology, as the manufacturing or reading of the beads does not entail sophisticated procedures, while the demand is anticipated to be very high.

In still another embodiment, multiple subsets of non-fluorescent microbeads are engineered, each subset tagged with numerous copies of a distinct single stranded DNA ('Control DNA, e.g. a gene; or a specific gene fragment; or an oligonucleotide representing a gene fragment). Numerous single strands of control DNA from each specific gene can be attached to the functionalized surface of a microbead as described above. Alternatively, oligonucleotides of a specific sequence can be attached on the microbead, or grown directly on the microbead using phosphoramidite chemistry which is established in the field of DNA synthesis. The size of this 'control cDNA' on the microbead surface can be of any length, but preferably such that it ensures maximum hybridization with a corresponding 'target cDNA' that has a complementary sequence. Large amounts of the same microbead carrying a single DNA sequence can then be manufactured. Next, a second microbead is selected and the process repeated for a second gene/fragment of interest. By repeating the procedure several times (e.g. 1,000 times), stocks of microbeads each carrying a unique DNA sequence are manufactured. The process can readily be automated.

As explained above, the gene immobilized on the microbead hybridizes to a labeled DNA, e.g., a 'fluorescently labeled target DNA', the hybridization produces a unique fluorescent signal which may be detected by the flow cytometer as the microbead passes through, and then the microbead is appropriately sorted. Therefore several millions microbeads emitting fluorescent signals, representing hundreds or thousands of diverse genes in the target DNA, can be rapidly detected and separated from non-fluorescent microbeads by this procedure.

A collection of individuals with a specific pathology can be screened for a common genetic trait (e.g. common set of unknown mutations/polymorphisms in an unknown set of genes) because the present invention allows the isolation and identification of only those genes that appear in common in the patient population. For example, for a set of 5 patients having early-age lung cancer, and for whom an inherited set of unknown mutated genes can be hypothesized.

DNA from a tissue sample (e.g. lymphoblasts) from each patient is extracted. The DNA is then enzymatically digested into small fragments (e.g.50–200 base pairs). Third, those fragments that contain polymorphisms (mutations) that appear as heterozygosities among the two alleles, are selected and isolated from the population of non-mutated DNA fragments. One preferred procedure to accomplish this task is the one described above using aldehyde-linker based methods, and will not be further addressed here. Another less preferred possibility is to utilize any other described technology that can 'capture' and isolate the heterozygous sequences, while discarding the non-mutant sequences. A combination of the above technologies is also possible. The 'target' DNA selected from each affected individual for polymorphism screening may be only from one gene; or preferably from several genes or from the whole cDNA library, or from the whole genome.

Following isolation of mutant fragments from each individual, the fragments are PCR-amplified using primers which are labeled with a fluorescent probe, or combination of probes. Thus, each of the 5 individual's mutant DNA is labeled with a different fluorescent probe from that of another member of the group, or combination of their probes, appropriate for flow cytometry (7-hydroxycoumarin; fluorescein; rhodamine; Texas Red; Bodipy; etc).

The fluorescently-labeled DNA from the 5 individuals is then mixed together and hybridized with microbeads engineered as described above. As described above, each subset of microbeads carries a specific gene (or gene fragment) as a 'control' DNA. Let us assume for simplicity that only one subset of microbeads is included, representing only one gene fragment. Each such microbead will allow target DNA from all 5 individuals to bind to it, if the corresponding gene fragment is mutated in all 5 individuals simultaneously. This microbead will emit all 5 fluorescent wavelengths when screened via flow cytometry, and therefore can be sorted and separated from microbeads with 4, 3, 2, 1 or none fluorescent emissions.

If instead of one, several subsets of microbeads representing numerous genes are utilized, the procedure remains unchanged. The flow cytometer will sort in the same container all microbeads (i.e. all genes, irrespective of their identity) that present fluorescent signals from a set percentage, e.g., all 5 fluorescent probes (i.e. genes from all 5 individuals). These are the genes of interest, i.e. the mutated genes that are likely to be the cause of the common disease in the patient population.

To discover the identity of these common genes, following flow cytometry the sorted microbeads are used in a PCR reaction to amplify the DNA fragments immobilized on them. By the design of the procedure followed for isolation of the mutant fragments, each fragment is flanked by the same, known PCR primers (see DFCI patent previously submitted). Finally, following PCR, the amplified fragments can be identified by a single application on a DNA microarray such as those that are currently commercially available, or preferably those described above.

Thus, the present procedure allows the isolation and identification of those mutated/polymorphic genes that appear in common in the affected patient population, and therefore have an increased probability to be related (or to be the cause) of the specific disease. Although the mutated/polymorphic genes in any single individual are likely to be many (e.g. 100,000 polymorphisms across the whole cDNA), the common genes are likely to be much fewer in number, since they must appear in common in all 5 individuals. The more individuals are simultaneously screened with the present method, the fewer the 'common' mutated genes are going to be, therefore the faster the 'disease genes' will be identified.

If more than 5 individuals are to be screened for common mutated genes with the present method, the flow-cytometric method again can be applied as follows: First, DNA from 5 individuals is fluorescently labeled and screened as described above. The sorted microbeads corresponding to genes mutated in all 5 individuals is then briefly treated to remove the fluorescence (e.g. via heating for 2 min, 96° C., to remove the fluorescent strand; or via an enzyme that removes the DNA segment containing the fluorescent probe; etc). These microspheres are then again processed via the same procedure, to screen 5 more individuals: they are mixed with the labeled DNA from these individuals, to hybridize to mutated genes; then they are sorted via flow cytometry to select those microbeads that emit all 5 fluorescent signals. These represent microbeads that have captured mutant genes both in the first and in the second set of 5 individuals, and they now represent genes that are mutated in all 10 (5+5) individuals. By repeating the procedure more individuals can be screened. Ultimately the number of sorted microbeads will decrease significantly, and should correspond to the few 'disease-specific genes' that are sought.

It is possible however that, although a mutated gene may be involved in the causes of cancer in most individuals, it is not required for cancer formation. Therefore it may only appear as a mutated gene in 80% of cancers. A significant feature of the present invention is that, apart from identifying genes that are mutated in all individuals, it also allows for mutated genes that appear in most but not all individuals to be identified. For example, flow-cytometric sorting of the microspheres can be adjusted so that if 2 out of signals, more preferably, 3 out of 5 signals are present in a single microsphere this is also selected in a separate container. One can readily select a particular cut-off percent. Similarly, if the mutated gene is present in 4 out of 5 individuals it will also be sorted, etc. In this manner, not only genes mutated in 100% of the patients, but also genes mutated in preferably 50%, or more preferably 60%, etc, will also be identified. Still more preferably the mutation is present in 80% of the members. Higher per centages will be seen when the group is composed of related individuals.

A practical advantage of utilizing flow cytometry and microbeads for the present approach is that, because the DNA is not immobilized on 'inflexible' DNA chips but on individual microbeads, the user has full control over which genes and controls will be included in his study, thereby the method can be adjusted to the needs of a particular application, on an experiment-by-experiment basis.

In an alternative application, instead of searching for common mututatios/polymorphisms in a patient population, common expression of specific sets of genes is sought (e.g. common genes up -or down-regulated in cancer tissues, or in a set of patients with susceptibility to lung cancer, etc).

To utilize the present invention for this purpose, a similar flow-cytometric analysis can be applied. Briefly, the cDNA generated from each individual is enzymatically fragmented, denatured and ligated with PCR primers tagged with a unique fluorescent probe, or combination of probes. The labeled, single stranded cDNA molecules from several individuals are then mixed together and incubated with microbeads designed and described above. The described flow-cytometric process is then applied to sort microspheres that present signals from all individuals simultaneously, signifying combined up-regulation of a specific gene in all individuals. Certain signal intensities can be selected as a 'threshold' above which a gene is considered as up-regulated (i.e. many copies bound to microbead) or down-regulated. Both commonly up-regulated and down-regulated genes in the population are bunched together and sorted in separate containers in this procedure. Therefore by following the protocol described above for deriving common mutations in the population, the genes that are up-regulated or down-regulated in common can also be identified.

Although flow cytometry is a preferred and very convenient embodiment of this invention, it has limitations as to how many fluorescent signals can be simultaneously detected each time a microsphere is measured, and how many different fluorophores can be used. With typical flow cytometers, 5–7 signals can be simultaneously measured; therefore each flow-cytometric measurement can readily detect common genes in 5–7 individuals, and the procedure can be repeated to screen additional individuals. For screening a population of 50 patients, the procedure typically needs to be repeated 7–10 times. Specialized flow-cytometers that can screen more than 5–7 signals simultaneously also exist, and these can increase the efficiency of this procedure.

Alternatively, the combined signals from microspheres can be detected with a different detection system, such as an ICCD camera, a microscope, or a photomultiplier that detects several wavelengths simultaneously.

Several control genes and microbeads can preferably be included in the flow-cytometric determination, in order to ensure each time that the method performs optimally.

In one embodiment, kits for carrying out the identification of these DNA mismatches with these beads can be sold. The kits would include the repair glycosylase, an X—Z—Y compound and preferably instructions. These materials can be in any vial. The materials can be in lyophilized form.

In a preferred embodiment, PCR primers would also be included.

In one preferred embodiment the following kit materials and instructions can be included:

Kit Formulation:
1. Isolate target and control cDNA.
2. Add PCR primers that contain a cleavable biotin at the end.
3. Mix target with control, cross-hybridize.
4. Bind sample to streptavidin-coated magnetic bead. (alternatively, streptavidin-coated microplates can be used).
5. With the sample immobilized on solid support, perform: hydroxylamine treatment/washing; Mut Y/TDG treatment(s)/washing; FARP/BARB/AED labeling/washing. Antibody labeling/washing; Chemiluminescence detection of mismatches. All these steps are very easy and convenient to perform with the DNA immobilized.
6. To recover sample and isolate the mutation-containing DNA, add DTT (see below) to break the S—S bond on the cleavable biotin.
7. Now apply the preparation on an appropriate solid support for the ligand compound chosen: (antifluorescein, streptavidin, succinimidyl-ester-coated plates for FARP, BARP and AED respectively). Remove unbound DNA, capture only mutated DNA.
8. Now collect mutated DNA from microplates. This can be done by several methods; e.g. adding 1 M of hydroxylamine to break the bond between the ligand and the DNA; or raising the temperature to denature captured DNA and collect the unmodified strand; or, in the case of cleavable —S—S—containing probes, simply add DTT to break the bond to the microplate.
9. Apply PCR using the primers inserted in step 2.
10. Detect mutated genes using the mutation detecting arrays described above using hybridization techniques.

In an alternative embodiment, the following protocol can be used:
1. Mixing the target and the control DNA (e.g. In a 1:1 ratio). The control DNA sequence is the wild type DNA corresponding to the target DNA sequence. The DNA can be whole or fraction of genomic DNA; or PCR-amplified portions of genomic DNA; or a cDNA library corresponding to the coding portions of the DNA. In the case that snps among the two alleles in cells of a single individual are examined, DNA from one allele is taken as 'the target', while DNA from the second allele is the 'wild type'.
2. Digesting the mixture into small double stranded fragments (e.g. 50–200 base pairs). Digestion can be done using one or more restriction endonucleases (e.g saui, alui, hpa-2, etc) at standard conditions (1 h, 37° C.). Digestion with enzymes that generate overhangs ('sticky ends') is preferred.
3. Hybridizing the target DNA with a control DNA sequence to create a duplex. The result of this hybridization is that mismatches occur at positions of SNPs and mutations. Self-hybridization of DNA from a single individual will automatically generate mismatches among fragments from the 2 alleles.
4. Ligating double-stranded linkers to both ends of the DNA fragments. Ligation is done via ligase, under standard conditions, using the sticky ends of the DNA fragments, or via established 5' end-ligation methods.
5. Crosslinking biotinylated mismatch repair enzyme (Mut Y) at the positions of mismatches on DNA, by following the procedure described above.
6. Isolating the biotinylated DNA fragments on avidin-coated magetic beads.
7. Pcr-amplifying the isolated DNA fragments, directly from beads, using the known primers ligated in step 4. The primers may be biotinylated if a chip DNA array is to be used in the last step.
8. The resulting end-biotinylated DNA sample can be hybridized directly on a chip mutation scanning array. The recognizable moiety can then be used to reveal gene regions that contain SNPs/mutations (e.g. Biotin-labeled DNA can be followed by fluoresceinated streptavidin, etc.).

The following examples are illustrative of the invention and are not limitations thereof.

EXAMPLE 1

Method for Large-Scale Detection of Base-Substitution Mutations in Cancerous Samples, Using One of the X—Z—Y Compounds, the FARP Marker Molecule (see FIG. 1)

Isolated mRNA from a cancerous tissue is transcribed into cDNA. Primers can be added to DNA at this stage for PCR amplification at a later stage (see FIG. 1). The sample is then hybridized with a corresponding wild-type sample of DNA to generate mismatch pairing at the positions of mutations. The hybridized DNA is treated with hydroxylamine to remove any aldehydes that may have formed spontaneously. The hybridized DNA sample is then treated with the Mut Y enzyme. Enzyme treatment recognizes A/G mismatches and upon recognition, depurinates the DNA and simultaneously generates an aldehyde at the site of mismatch. The DNA is then treated with the labeling compound AED or FARP or BARP to generate a covalent oxime bond at the position of the mismatch. Upon labeling, the DNA is immobilized on microplates appropriate for the specific labeling compound and excess, unlabeled DNA is washed away. The DNA labeled at mismatch sites can now be analyzed by a variety of methods including detection of total mutations by chemiluminescence or identification of labeled genes via DNA arrays.

Materials and Methods

1) DNA, Oligomers and Chemicals

FARP [5-(((2-(carbohydrazino)-methyl)thio)acetyl)-aminofluorescein, aminoxyacetyl hydrazide, Fluorescent Aldehyde Reactive Probe] was synthesized as described (Makrigiorgos G M, Chakrabarti S and Mahmood S. Int J Radiat Biol, 74: 99–109, 1998). High purity genomic calf thymus DNA and double stranded ladder (pUC18 Msp I digest, 27–500 base pairs) was purchased from Sigma Chemical and used without further purification. Single stranded (+strand) M13 DNA was purchased from Pharmacia Biotech and pGXIs14 plasmid DNA, a gift from Professor MacLeod, M D, Anderson Cancer Center, was isolated from the host bacteria as described earlier (Makrigiorgos G M, Chakrabarti S and Mahmood S. *Int J Radiat Biol,* 74: 99–109, 1998). Both agarose gel electrophoresis and the absorbance ratio at 260 nm to 280 nm were performed to determine the purity of the plasmid. Gel purified 49-mer oligonucleotides representing the TFIIIA transcription factor-binding sequence of the Xenopus rRNA gene (enumerated in Table 1, at the end of this Example) were supplied by Oligos Etc Inc. Enzyme Mut Y (*E. coli*) was purchased from Trevigen Inc. and stored as recommended by the manufacturers. Hydroxylamine purchased from Sigma Chemical was already freshly made prior to the experiments. GTG agarose was obtained from FMC Bioproducts, polyacrylamide gel electrophoresis reagents were from National Diagnostics while SYBR GOLD nucleic acid gel stain and PicogreenΘ DNA quantitation dye was supplied by Molecular Probes. For chemiluminescence studies, Reacti-Bind NeutrAvidin coated polystyrene plates (pre-blocked with Bovine Serum Albumin) were supplied by Pierce. Anti-fluorescein-Fab fragments (Sheep)-alkaline phosphatase conjugate (antiF-AP) was purchased from Boehringer Mannheim. CDP-Star, a 1, 2 dioxetane chemiluminescent enzyme substrate and Emerald-IIΘ enhancer used with CDP-star was purchased from TROPIX. Micro Bio-Spin G25 chromatography columns were obtained from Bio-Rad laboratories. Label ITΘ Nucleic Acid biotinylation kit was purchased from PanVera Inc. All reagents and buffers were of analytical grade and made with ultrapure water (1800 Mohm $m^{-1}$ resistivity) delivered by an Alpha-Q system (Millipore).

2) Acidic or Physiological Depurination of Calf Thymus DNA. Treatment with Hydroxylamine Aldehyde containing apurinic/apyrimidinic (AP) sites were chemically induced in calf thymus or plasmid DNA by a short exposure (0–60 seconds) to acidic conditions (pH=3.5) over a set time period at a temperature of 38° C., as described (Makrigiorgos G M, Chakrabarti S and Mahmood S. *Int J Radiat Biol,* 74: 99–109, 1998). The reaction was halted by placing the sample quickly on ice and adding a neutralization solution (10% of 3M sodium acetate and 1M potassium phosphate buffer at pH 7 and 7.5 respectively), to final volume of 50:1. AP sites were also slowly generated in calf thymus DNA via spontaneous depurination at 37° C., pH=7.0, over a period of days, and these were monitored with the present assay. Prior to incubation at 37° C., the DNA was treated with 5 mM hydroxylamine for 1 hour at room temperature to remove traces of existing aldehydes from the pool of potential FARP-binding sites. The hydroxylamine was then removed via G25 ultracentrifugation and the sample was resuspended in sodium phosphate buffer, pH 7.

3) FARP-trapping of Aldehydes and Subsequent DNA Biotinylation.

To covalently trap open-chain aldehydes generated in DNA at the position of AP sites, 500 :M FARP was reacted with 0.05–2.5:g of DNA in 40 mM sodium citrate pH 7.0 at 15–22° C., for 30 minutes. Non-covalently bound FARP was removed by G25 ultracentrifugation. FARP-labeled DNA was either used on the same day or stored at 4° C. or –20° C. for a few days, prior to further experiments. To immobilize FARP-labeled DNA on neutravidin microplates, the DNA was exposed for one hour to a commercially available biotinylation reagent (Biotin Label IT™ reagent, 1:1; reagent per :g DNA, in MOPS buffer, pH 7.5 at 37°). Excess reagent was them removed by G25 ultracentrifugation. The samples were either used immediately or stored at 4° C. for a few days, prior to chemiluminescent studies.

4) Chemiluminescence Measurement of FARP-trapped Aldehydes in Calf Thymus or Plasmid DNA.

Double stranded DNA, doubly labeled with FARP and biotin, was immobilized on neutravidin-coated microplate strips in the presence of 5 nM antiF-AP. 30–50 ng of doubly labeled DNA plus 5 nM antiF-AP in a total of 50:1 was incubated at room temperature for one hour in TE pH 7.5. Unbound sample and antiF-AP were removed by pipeting and washing with TE at least four times. The microplate strips were then transferred in to 50 ml polypropylene tubes and washed four times in 30 ml–50 ml of TE buffer with constant agitation for 10 minutes. The chemiluminescent substrates(CDP-Star plus Emerald II enhancer) were then added in 0.1 M diethanolamine, pH 8.5 and the anti-F-AP-catalyzed reaction was carried out at room temperature for 1 hour, after which maximum light generation was achieved. In separate experiments, to quantitate the fraction of biotinylated DNA captured on microplates PicogreenΘ dye was used to measure double stranded DNA just prior and after its removal from neutravidin-coated plates.

5) Chemiluminescence Instrumentation

The low light from the chemiluminescence reaction was detected using an intensified charged coupled device (ICCD) system (Princeton Instruments). This ICCD camera utilizes a proximity focused microchannel plate (MCP) image intensifier, fiber-optically coupled to the CCD array. The entire area of the ICCD is capable of light detection, giving a total of 576×384 pixels on a Pentium® PC computer screen. Both the intensifier and CCD are cooled to −35° C. thermoelectrically and the dark current is less than 50 counts per minute. The ICCD was used to detect total light generation from each cell of the microplate strip. Cells were individually placed in a reproducible geometry at ~2 mm distance from the ICCD and the total light output per second measured. The background chemiluminescence (signal measured when FARP was omitted from the procedure) was subtracted from all samples. All measurements were repeated at least three times.

6) Formation of Homoduplex and Heteroduplex Oligonucleotides.

49-mer oligonucleotides and their complementary strands with or without a centrally located T-to-G base substitution were synthesized. In another synthesis of the same oligomers, 5' biotinlyated 49-mers and their complementary unbiotinylated strands were synthesized (Table 1). For hybridization, equimolar amounts (~0.5 :g) of each oligonucleotide were annealed in 40 mM Tris-HCl (pH 7.5), 20 mM $MgCl_2$ and 50 mM NaCl to form duplex oligonucleotides. The mixture was first heated to 95° C. for 2 minutes, then allowed to hybridize at 65° C. for 3 hours and cooled slowly to room temperature. Following hybridization, the double stranded 49-mers were treated with hydroxylamine (5 mM in citrate pH 7.0, for 30 minutes, 25° C.) to remove traces of spontaneously or heat-generated aldehydes from the pool of FARP-reactive sites.

7) Treatment of M13 DNA, Ladder DNA and Duplex Oligonucleotides with Mut Y and TDG and Gel Electrophoresis:

50 ng of the test DNA (single stranded M13, ladder DNA, or duplex oligonucleotide were incubated for 1 hour, 37° C. with 1.0 unit Mut Y in 40 mM Na-citrate buffer (pH 7.0) and then alkali treated to concert positions of missing adenine to strand breaks. Analysis of cleavage products for single stranded M13 DNA was done by agarose gel electrophoresis 0.9% agarose, run overnight at 20 V in 1×TBE buffer and stained with 1:g/ml ethidium bromide). Fragment analysis for ladder DNA and oligonucleotides was done by 16% denaturing polyacrylamide gel electrophoresis in the presence of 7.5M urea at 20 V/cm. The DNA fragments were detected by SYBR Gold dye or by ethidium staining and photographs taken by Eagle Eye™ Still Video (Stratagene).

8) Chemiluminescence Measurement of FARP-trapped Mismatches in Oligonucleotides, Ladder and M13 DNA.

M13 DNA, ladder DNA, or 5'-biotinylated oligonucleotide duplexes, hydroxylamine-treated, were exposed to Mut Y, FARP-labeled biotinylated with the protocols described above. The biotinylation step was omitted for the oligonucleotides since these were pre-biotinylated In some experiments, samples were kept at 70° C. for 8 minutes to inactivate the enzyme at this stage. Typically 50 ng from the doubly (biotin plus FARP) labeled nucleic acids were applied on neutravidin-coated microplates and their chemiluminescence measured.

Results

Figure 2:
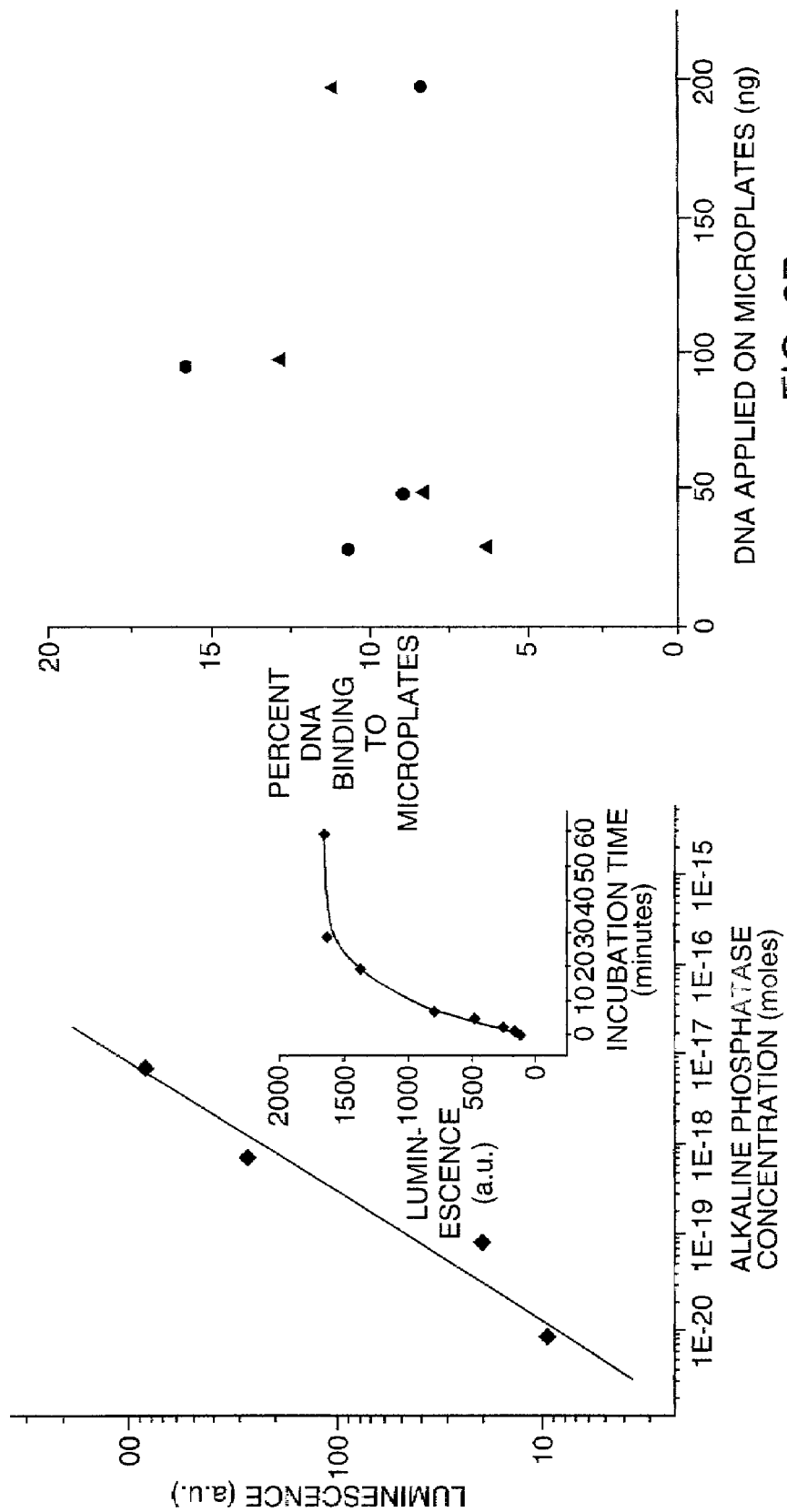
FIG. 2 shows the sensitivity of chemiluminescence detection of alkaline phosphatase with a cooled ICCD camera. The inset shows time-dependent buildup of chemiluminescence following addition of chemiluminescent substrate plus enhancer.

1) Dual Labeling of DNA and Chemiluminescence Detection Using the Present Protocol FIG. 2 shows chemiluminescence obtained with the present setup when serial dilutions of free alkaline phosphatase were added to CDP-Star® substrate and Emerald II enhancer and measured using the cooled ICCD. The chemiluminescence detection limit of this set up is less than 0.01 attomoles alkaline phosphatase. Examination of the buildup of alkaline phosphatase chemiluminescent signal in solution following mixing with substrate plus enhancer at room temperature, demonstrates that after 60 minutes a relatively constant value is achieved (FIG. 2, inset). Therefore all measurements reported were conducted 60–80 minutes following addition of the substrate. To estimate the fraction of biotinylated DNA captured on the neutravidin-coated microplates, biotinylated DNA was quantitated using the fluorescence of Picogreen™ dye prior to its application and immediately following removal of unbound DNA from microplates (not shown). 49-mer oligonucleotides resulted in approximately 10% capturing on the plates while of the 50–100 ng high molecular weight calf thymus DNA less than 2% was immobilized on the plates, possibly due to secondary structures and associated steric hindrances.

2) Ultrasensitive Detection of Aldehydes in DNA

Figure 3:
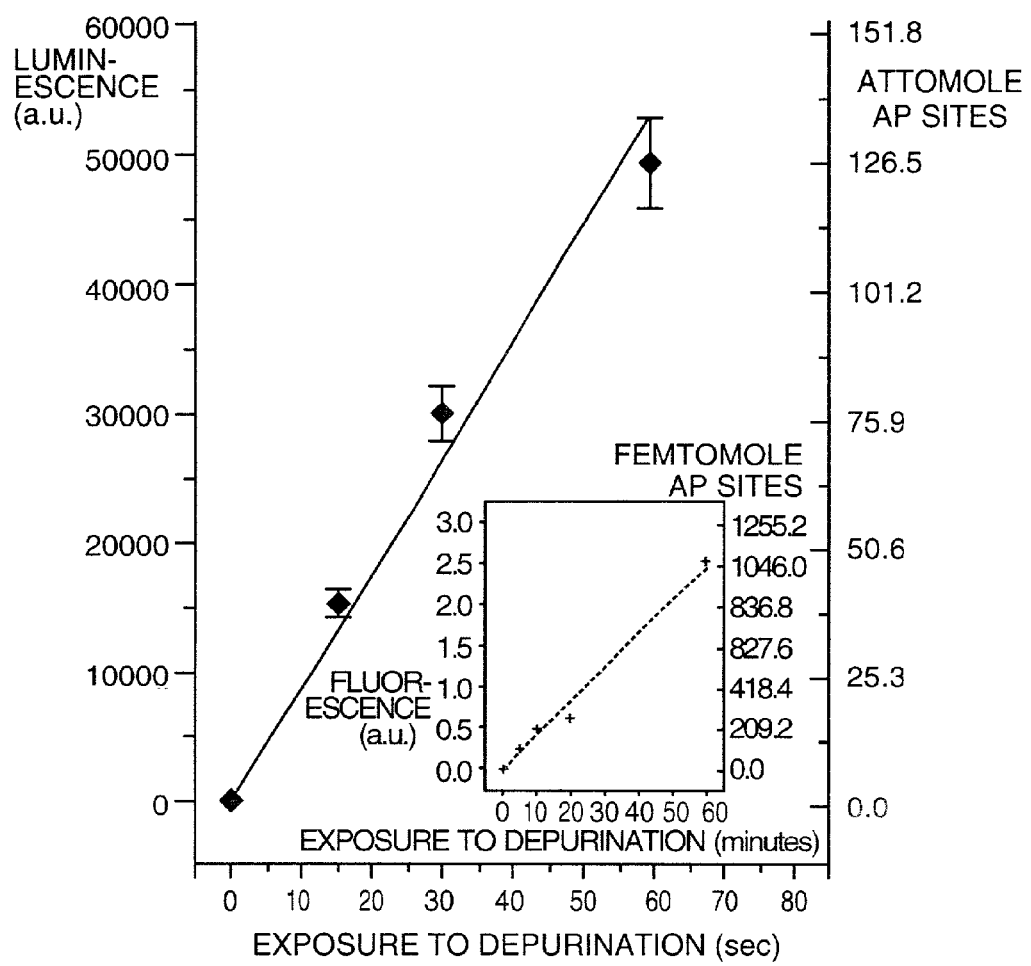
FIG. 3 shows chemiluminescence detection of aldehyde-containing apurinic/apyrimidinic (AP) sites generated in plasmid DNA following depurination in sodium citrate, pH 3.5 at 38° for up to 60 seconds. The inset depicts fluorescence detection when extensive depurination under identical conditions is applied. Data in the inset (from us (Makrigiorgos GM, Chakrabarti S and Mahmood S. Int J Radiat Biol, 74: 99–109, 1998) were used to convert chemiluminescence units to AP sites (right axis, see text).

Chemiluminescence detection of aldehyde-containing AP sites generated in 100 ng plasmid DNA following depurination in sodium citrate, pH 3.5 at 38° C. for up to 60 seconds and trapping of AP sites by FARP is depicted in FIG. 3. The induction of luminescence is linear with respect to depurination exposure. The inset, from an earlier work (Makrigiorgos G M, Chakrabarti S and Mahmood S. Int J Radiat Biol, 74: 99–109, 1998), demonstrated detection of fluorescence following FARP-labeling of this same plasmid exposed under identical conditions to higher depurination times (0–60 minutes). The fluorescence-based approach is less sensitive than the present method, however, it allows direct quantitation of the number of FARP molecules per DNA base pair. Five minutes depurination under the same protocol yields approximately 1 AP site per 34,000 bases (Makrigiorgos G M, Chakrabarti S and Mahmood S. Int J Radiat Biol, 74: 99–109, 1998). Assuming a linear decrease of AP sites for lower depurination exposures, the 15 second exposure in FIG. 3 corresponds to approximately 1 AP site per $7 \times 10^5$ bases. The amount of microplate-captured DNA generating this signal is approximately 1–2 ng. Therefore the absolute number of AP sites recorded following 15 seconds depurination is approximately 5 attomole (see right axis in FIG. 3).

Figure 4A:
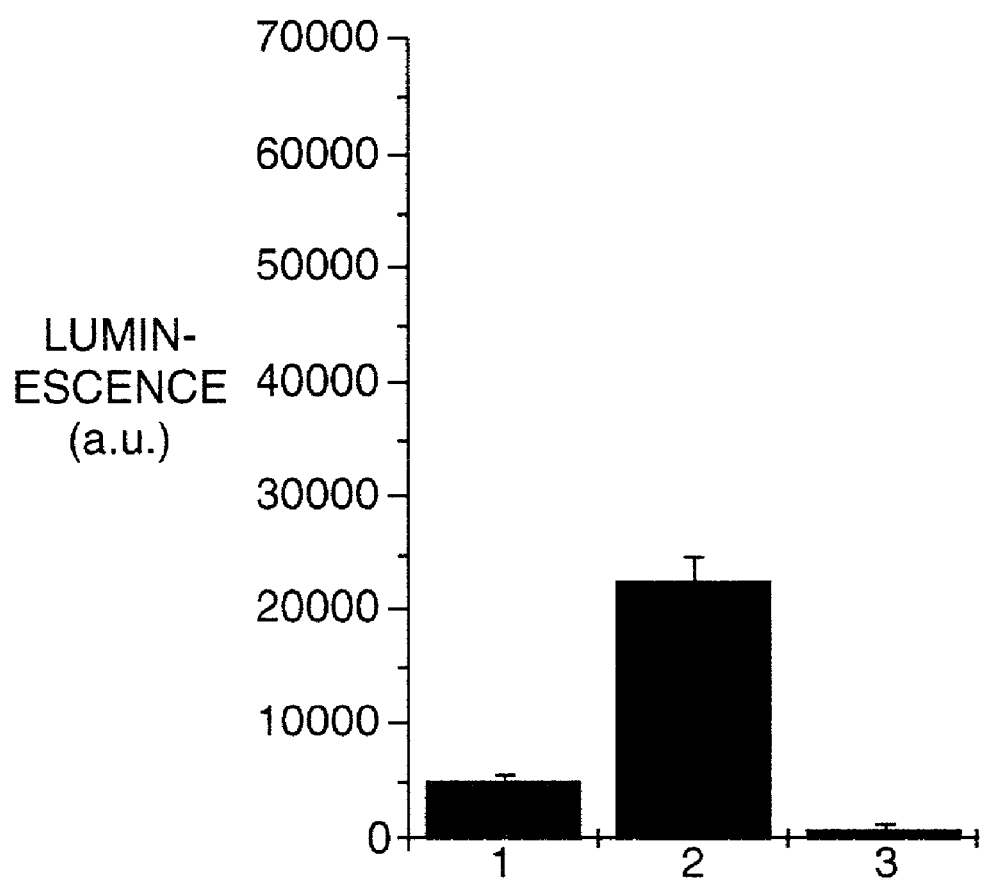
FIGS. 4A and 4B shows sensitive detection of AP sites using FARP.
Figure 4B:
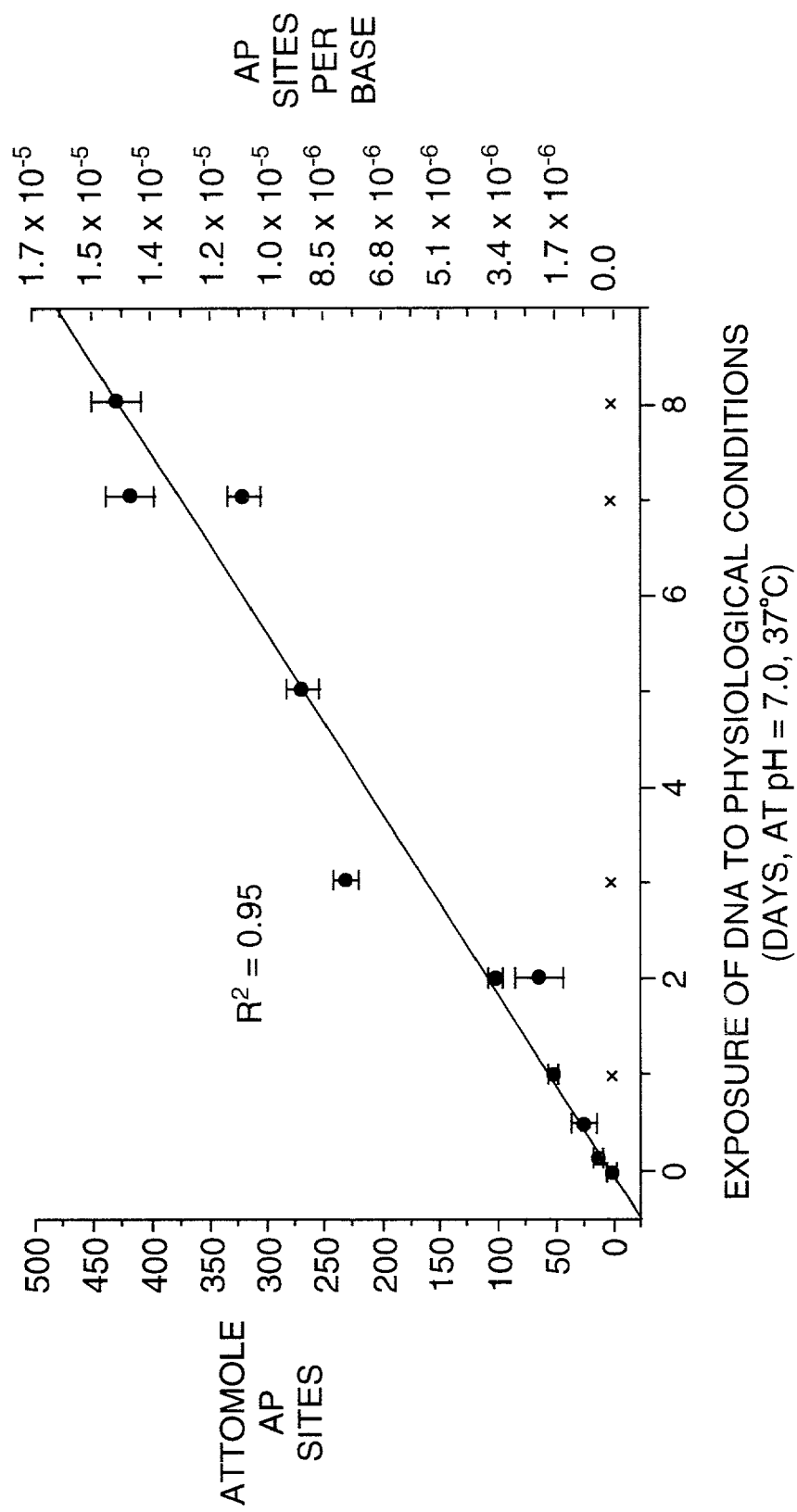

To estimate the lowest number of AP sites detectable, hydroxylamine treatment of genomic calf thymus DNA was first employed in order to remove traces of spontaneously-generated AP sites (e.g. AP sites expected to be present in genomic DNA from mammalian cells prior to DNA extraction plus AP sites generated during handling). Hydroxylamine is a small molecule and is expected to react rapidly with aldehydes, as previously demonstrated for methoxyamine (Talpaert-Borle M, and Liuzzi M. *Biochimica Biophysica Acta*, 740: 410–416, 1983), thereby prohibiting subsequently added FARP to react at the same positions. FIG. 4A depicts the decrease in the chemiluminescence signal obtained following hydroxylamine treatment of genomic calf thymus DNA depurinated for 15 seconds. Following hydroxylamine removal and reaction with FARP, the chemiluminescence was reduced to almost background levels. When hydroxylamine-treated calf thymus DNA was kept at 37° C., phosphate buffer pH=7, and assayed for AP sites via FARP as a function of time, a linear increase in spontaneously-generated aldehydic AP sites was detected (FIG. 4B). DNA kept at 4° C. under similar conditions did not display any luminescence signal (FIG. 4B). According to FIG. 4B, the limit of detection by the present microplate-based method is ~0.2 attomole AP sites, or 1 AP site per 2×10⁷ bases, using a starting DNA material of about 100 ng.

3) Gel Electrophoresis of Mut Y-treated Oligonucleotides and Single Stranded M13 DNA.

49-mer oligomers engineered to form a double stranded structure, with or without a centrally located A/G mismatch upon hybridization, were exposed to Mut Y, alkali treated and examined upon denaturing gel electrophoresis. Generation of the two expected fragments was observed for the heteroduplex oligomers, while no cutting as present in the homoduplexes (FIG. 5A). Under the conditions applied, the fragmented DNA appears to be less than 50% of the total DNA per lane, which would result if all A/G mismatches were reacted upon by Mut Y. The homoduplex-containing double stranded DNA ladder (27–500 base pair fragments) did not demonstrate additional fragmentation following enzymatic treatment (FIG. 5B). In contrast, Mut Y treatment of the 7249 base-long M13 single stranded DNA resulted in the generation of approximately 6 fragments, the largest of which is about 1000 bases long, as demonstrated in lane 5, FIG. 4C. Generation of Mut Y-recognized sites in the single stranded high molecular weight DNA is attributed to sequence self-complementation generating transient mismatches. It can be inferred that, to generate 6 discrete fragments, and assuming a less than 100% efficiency of Mut Y in cutting each site, an average of 3 Mut Y-recognized cutting sites are generated per each 7249 base-long M13 molecule.

4) FARP-based Chemiluminescence Detection of Mismatches in High and Low Molecular Weight DNA.

Figure 6:
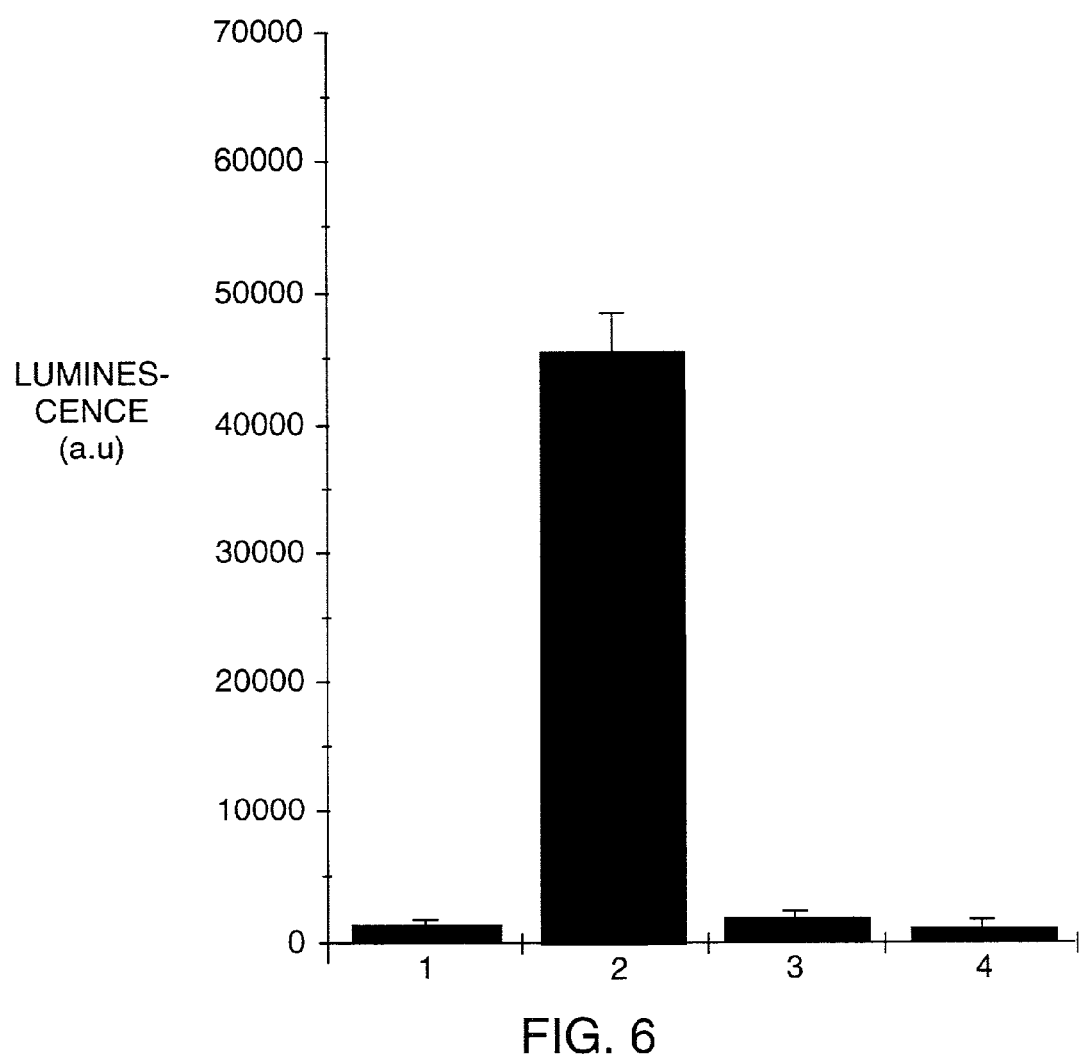
FIG. 6 shows FARP-based chemiluminescence detection of Mut Y-treated DNA of a single length: 49-mer oligonucleotides are enzymatically-treated, FARP-labeled and captured on microplates. Bar 1, A/G mismatch, no Mut Y. Bar 2, A/G mismatch, plus Mut Y. Bar 3, No mismatch, no Mut Y. Bar 4, no mismatch, plus Mut Y.
Figure 7:
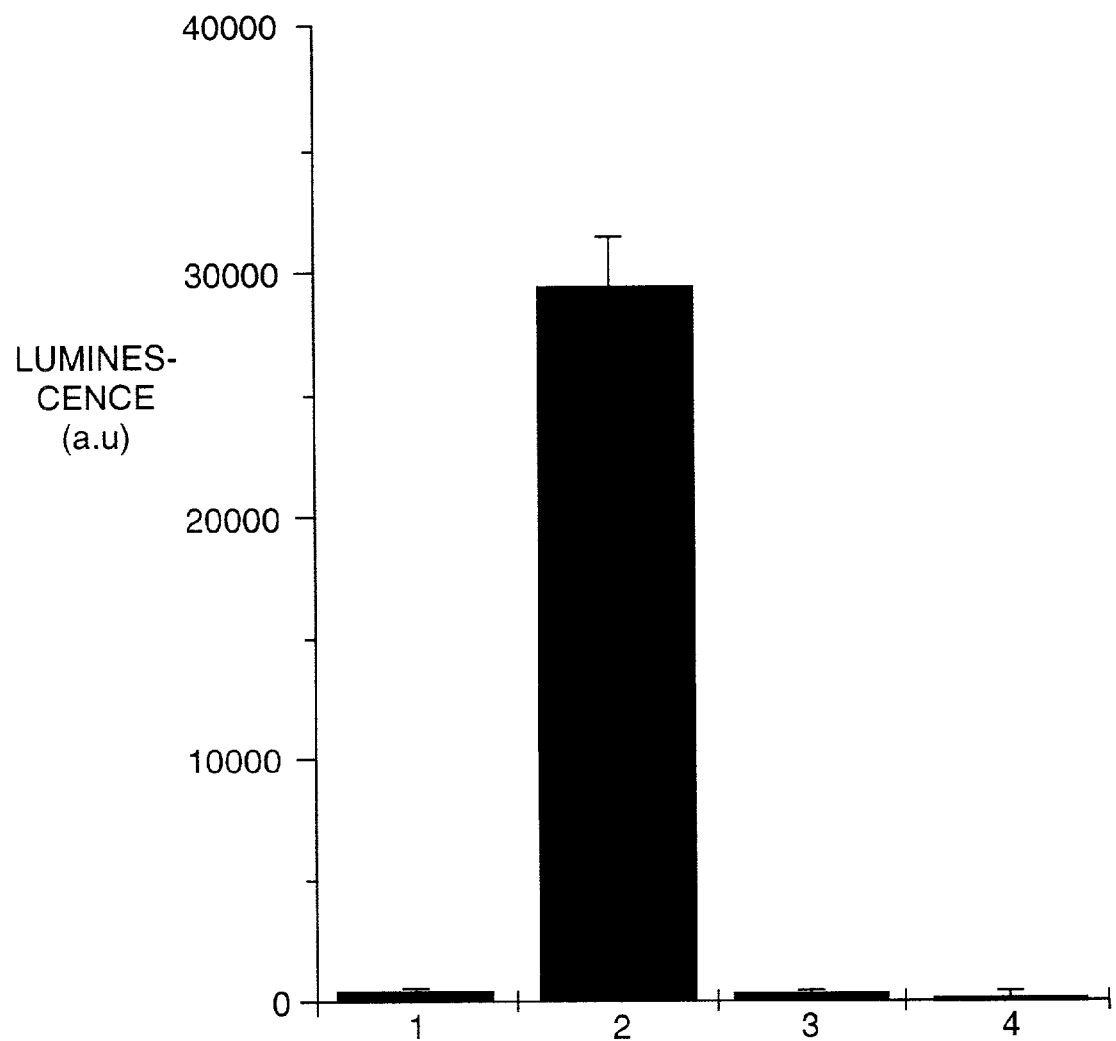
FIG. 7 shows FARP-based chemiluminescence detection of Mut Y-treated DNA fragments of varying length: Single stranded M13 DNA (7249 bases) and double stranded homoduplex mixtures (DNA ladder, 27–500 base pairs) are enzymatically-treated, FARP-labeled and captured on microplates. Bar 1, M13 DNA, no Mut Y. Bar 2, M13 DNA, plus Mut Y. Bar 3, ladder DNA, no Mut Y. Bar 4, ladder DNA, plus Mut Y.

Starting with 100 ng of biotinylated 49-mer homoduplexes or heteroduplexes, the nucleic acid was treated successively with hydroxylamine, Mut Y, then FARP and applied on neutravidin microplates for chemiluminescence detection of mismatches. A strong signal was obtained for A/G mismatch-containing oligonucleotides (FIG. 6), while no signal was obtained when Mut Y was omitted, or when oligonucleotides without mismatch were Mut Y-treated. A mixture of double stranded homoduplexes (DNA ladder) treated in the same way also demonstrated absence of chemiluminescence signals (FIG. 7). In contrast, single-stranded M13 demonstrated a chemiluminescence signal of about 100 times the signal obtained without Mut Y indicating the generation of FARP-reactive sites following Mut Y treatment (FIG. 7). The chemiluminescence results agree with the fragmentation results obtained by gel electrophoresis (FIG. 5).

1 and 2 are complementary and form a homoduplex. 1 and 3 form a heteroduplex with and A/G mismatch at position 20. In a separate set of oligonucleotides, a biotin molecule (B) was incorporated at 5' end during synthesis.

EXAMPLE 2

BARP-Based Detection of Mismatches Formed via Self-Complementation of Single Stranded M13 DNA Samples of M13 single stranded DNA that contain approximately 1 Mut Y-recognizable mismatch per 2,500 bases were treated with Mut Y to generate aldehyde-containing reactive sites appropriate for reaction with BARP. Nominal gel electrophoretic studies as well as BARP-based chemiluminescent studies were then preformed. Control samples used were: Single stranded M13 without enzymatic treatment; Double stranded M13 DNA without any mismatches and no enzyme treatment; and double stranded M13 DNA without mismatches and enzyme. FIG. 8 (A and B) shows the results of both methods of detection. FIG. 8A (luminescence studies) show that only when mismatches are present (single stranded M13) and Mut Y is used is there a chemiluminescence signal. In agreement, gel electrophoresis (FIG. 8B) shows cuts in M13 are only generated under the same conditions. It can be seen that there is good agreement among the two methods. As described, the method is highly specific for mismatch-containing DNA, i.e. DNA without mismatches, or DNA with mismatches but no Mut Y generate no signals.

EXAMPLE 3

Detection and Isolation of DNA Containing Base-substitution Mutations: Detection of a Single A-to-C Transversion Engineered in a P53 Gene Within A 7091-Long Plasmid The ability of the present technology (A.L.B.U.M.S) to detect base mismatches (demonstrated in previous examples) is directly applicable to detection of base substitution mutations. For example, a standard procedure to generate mismatches at the positions of mutations in DNA, is to mix mutation-containing DNA with wild-type DNA. Upon heating and re-hybridization of the mixture, heteroduplexes with mismatches are generated at the positions of mutations (FIG. 1), which can then be detected with high sensitivity and specificity as demonstrated in example 1.

To isolate mutation-containing DNA from normal DNA, following BARP-labeling of the generated aldehydes at

TABLE 1

Sequences of the synthesized oligonucleotides

1. B-5'-GTC TCC CAT CCA AGT ACT AAC CAG GCC CGA CCC TGC TTG GCT   (SEQ ID NO:1)
TCC GAT T-3'

2. B-5'-AAT CGG AAG CCA AGC AGG GTA GGG CCT GGT TAG TAC TTG GAT   (SEQ ID NO:2)
GGG AGA C-3'

3. B-5'-AAT CGG AAG CCA AGC AGG GTA GGG CCT GGG TAG TAC TTG GAT   (SEQ ID NO:3)
GGG AGA C-3' positions of mismatches (FIG. 1) the DNA is immobilized on neutravidin-coated microplates, followed by exhaustive washing to remove the homoduplex DNA. As a result, only BARP-containing DNA is retained on the plates, thereby isolating mutant DNA.

To recover the purified mutation-containing DNA from the microplate, the samples can be either heated 2 min at 96° C. or treated 1 min with NaOH to denature the DNA and recover the non-covalently modified strand, which is then used for amplification via PCR. The following section detail the procedure.

A 7,091 bp long plasmid that incorporates the full-length human cDNA p53 sequence (1,691 bp) was engineered to contain base substitutions, via site-specific mutagenesis. The present technology was used to detect a known A-to-C base substitution mutation engineered in codon 378 within the plasmid-incorporated p53. Circular plamids (1 µg) containing mutant p53 genes were treated with a 5'-CG/CG-3' cutting enzyme (BstU I, Sigma, 1 unit, 1 h, 37° C.) to generate linear fragments (~400 to 2,500 bp), followed by a 10 minute, 70° C. treatment to inactivate the enzyme. The mutant-containing sample (1 µg) was mixed (1:1) with a similarly treated normal p53-containing sample, heated (96° C., 2 minutes) and hybridized overnight, at 65° C. to generate A/G (25%), and T/C (25%) mismatches at p53 codon 378, as well as homoduplex p53 and plasmid fragments.

Figure 9B:
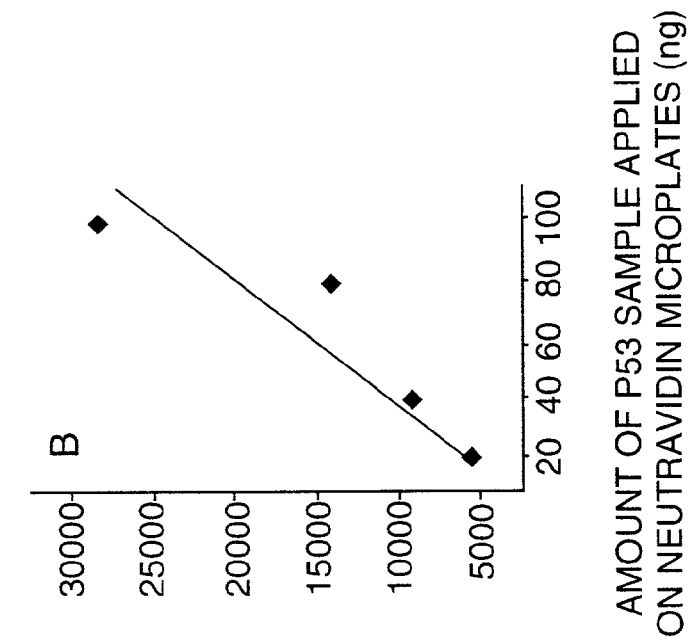
FIGS. 9A and 9B show detection of a mutation.
Figure 9A:
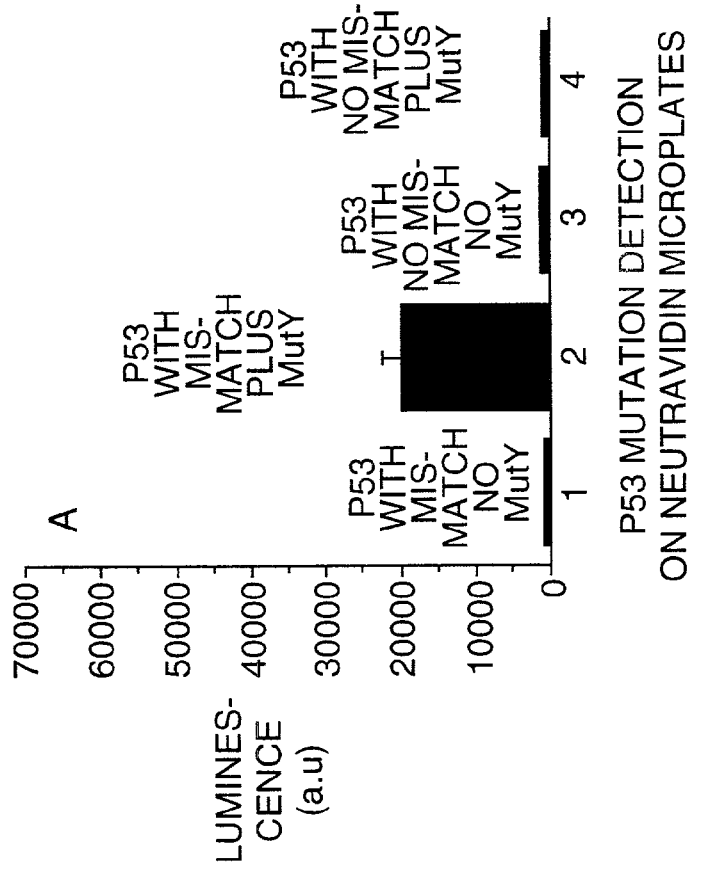

To detect the presence of the mutation via ALBUMS, 100 ng of the mismatch-containing DNA mixture (p53 plus plasmid fragments) was treated exactly as described for the M13 treatment in example 2: (a) hydroxylamine treatment and removal, (b) Mut Y treatment and BARP-binding, (c) fluoresceination and (d) binding to neutravidin plates and chemiluminescence detection. FIG. 9A demonstrates that strong signals are observed when the mutation is present, while background signals are obtained from normal p53-containing plasmid (i.e. complete lack of false positives). FIG. 9B shows variation of signals versus DNA amount applied on microplates. These data represent an average of 4 independent experiments.

In conclusion, the present technology (A.L.B.U.M.S) allows a sensitive and specific detection of 1 base substitution mutation within a 7,091 bp-long, p53-containing plasmid with a virtual absence of false positives (defined as signal when no mismatch is present, FIG. 9A). Unequivocal detection of a single base substitution within a 7,091 long plasmid cannot easily be conducted with any of the existing methodologies (Nollau P and Wagener C. Clinical Chemistry 43: 1114–1128, 1997). ALBUMS on the other hand can detect the mutation on a microplate with minimal sample (<100 ng) and effort involved. Following formation of heteroduplexes, the procedure is currently completed in 6 hours, requires no special equipment or laborious handling and can be automated on microplates so that 96 samples can be examined at once. To achieve a similar result using conventional sequencing would not be possible (Primrose SB, Principles of Genome Analysis, Chapter 5, Sequencing Methods and Strategies, p125, Second Edition, Blackwell Science Ltd., Oxford, UK).

EXAMPLE 4

Comparison of Small Versus Large Ligand Compounds in Binding to Mut Y or TDG Generated Reactive Sites in DNA: Synthesis and Advantage of AED Versus BARP AND FARP. Chemiluminescence Signals by AED To synthesize AED, O-(Carboxymethyl)hydroxylamine hydrochloride was conjugated to ethylenediamine (Aldrich) in distilled water using 1-Ethyl-3-[3-(dimethylamino)propyl] carbodiimide (EDAC) as the coupling reagent. An 100-fold excess of ethylenediamine over O-(Carboxymethyl)hydroxylamine hydrochloride was utilized during the reaction to allow preferential coupling of ethylenediamine to the carboxyl groups. The conditions for the catalysis of this reaction by EDAC is well known to those skilled in the art. TLC analysis and purification on silica gel with $CHCl_3$:$CH_3OH$:$CH_3COOH$ in a 70:20:5 ratio indicated the product at an $R_f$ of 0.2–0.25. The certificate of analysis provided 1H NMR data consistent with the AED structure provided earlier.

Figure 10A:
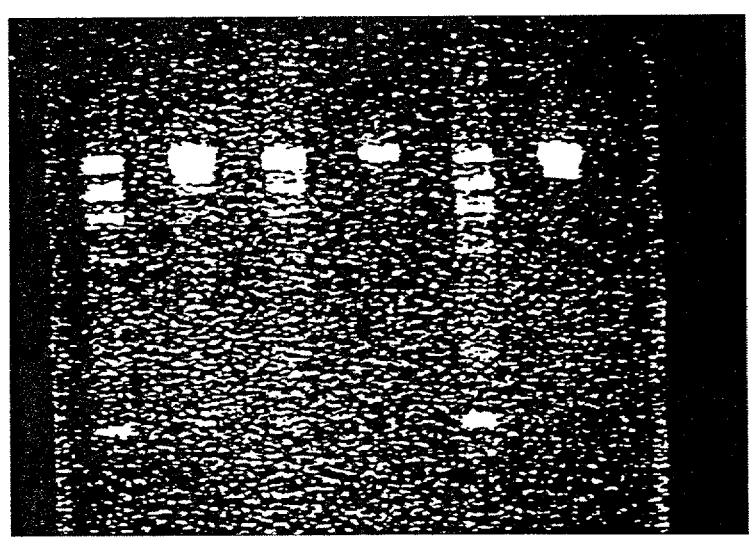
FIGS. 10A and 10B compare DNA binding by different compounds.
Figure 10B:
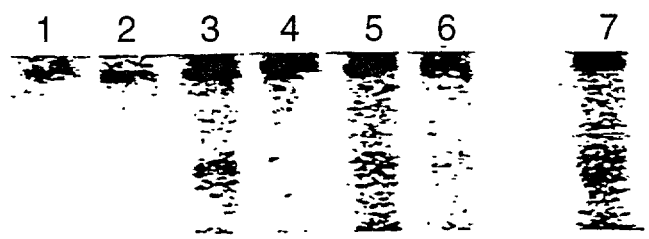

(b) The ability of hydroxylamine-based compounds (e.g. FARP, AED, BARP, or methoxyamine) to bind reactive sites in DNA can be tested with a simple experiment. It is well known that, if hydroxylamine-compounds (such as methoxyamine) are covalently bound to aldehyde-containing abasic sites in DNA, then treatment with alkali (NaOH) cannot generate a strand break at the position of base loss (-otherwise a cut is generated). This simple observation allows direct testing of ligand binding to DNA following Mut Y-treatment of the nucleic acid (FIG. 10A) or TDG-treatment of nucleic acid (FIG. 10B). Mismatch-containing single-stranded M13 DNA was subjected to Mut Y to generate aldehyde containing abasic sites, and then alkali-treated to generate fragments at the positions of mismatches. Lane 2, in FIG. 10A (agarose gel stained with ethidium bromide and photographed under UV light) demonstrates the generated fragments. In lanes 3, 4, 5, and 6, during Mut Y incubation the following ligand compounds were also included: 5 mM methoxyamine, 5 mM AED, 10 mM AED or 5 mM BARP respectively. As expected, the very low molecular weight compound methoxyamine prevents formation of any fragments, indicating a 100% binding to all reactive sites formed. Also, AED (bands D and E) demonstrates an almost complete binding to the reactive sites, especially when 10 mM is used (Lane E). In contrast, BARP can only prevent to a very small degree the formation of bands, indicating a very low (<5%) binding affinity to the reactive sites.

Similarly, in FIG. 10B, the TDG enzyme was used (TDG recognizes mismatched thymine and generates an aldehyde at that position following excision of thymine). Oligonucleotides with a G/T mismatch were synthesized (lanes 1, 2, oligos alone) and exposed to TDG in the absence (lanes 3) or in the presence of 5 mM methoxyamine (lane 4), 5 mM BARP (lane 5), 5 mM AED (lane 6) or 0.5 mM FARP (lane 7). It can be seen that the cuts generated by TDG (lane 3 lower band) are not present when methoxyamine (lane 4) or AED (lane 6) are included in the reaction, demonstrating the binding of these compounds to the mismatches. BARP and FARP on the other hand (lanes 5 and 7) demonstrate significantly lower binding, since the lower band is present.

In conclusion: (a) AED is almost as efficient as methoxyamine (100%) in binding the Mut Y-generated reactive sites. (Methoxyamine itself however cannot be used in the present application because, unlike AED, following binding it allows no further derivatization as it has no secondary binding site available for antibody binding). (b) BARP only shows little (<5%) binding; despite that, and because the present method is extremely sensitive, high chemiluminescence signals are still generated with BARP when mismatches are present, as shown in the previous example. The same is valid for FARP.

(c) The ability of DNA-bound AED to be recognized by a secondary ligand and then by an antibody, as described in the Detailed Description section of this invention was demonstrated by the following. The free primary amine (—NH2 group) of AED was covalently bound to biotin by addition of 1 mM biotin-LC-succinimidyl ester (Pierce) in 0.1 M sodium bicarbonate, pH=8.5 for 2 h. The conjugate was purified by ultracentrifugation through 2 G25 filters (Pharmacia), fluoresceinated by using the Mirus fluoresceination reagent (Panvera Inc, see example 1) and then applied on neutravidin microplates. Addition of antifluorescein-AP antibody generated a strong chemiluminescence signal (FIG. 12) in the sample treated with Mut Y enzyme (i.e. aldehydes were generated), but not in the sample not-treated with Mut Y (aldehydes not generated).

EXAMPLE 5

Labeling of Mismatches with FARP, BARP or AED: Inactivation of Enzymatic Action During Labeling A DNA sample containing mismatches is dissolved in a buffered solution and treated with a repair glycosylase, either Mut Y or TDG (1 unit enzyme per µg DNA). The reaction is incubated at 37 C. for 1 hour. Upon completion of the reaction with Mut Y or TDG, the solution is cooled to 15° C., to arrest enzymatic activity. FARP is added to the sample and allowed to react for 30 minutes at 15° C. At the end of the 30 minute incubation with FARP, the reaction solution is suddenly heated to 70° C. for two minutes to inactivate the enzyme. The sample of DNA is now ready for purification and detection as previously described. Alternatively, instead of heating to 70° C. the enzyme can be solubilized and removed via a standard phenol-chloroform extraction, or via addition of Proteinase K (0.1 mg/ml, 2 h, 37° C.).

EXAMPLE 6

Strategy to Utilize DNA Chips for Detection of Both Inherited Polymorphisms and Mutations, As Well as Acquired Mutations from Cancer Samples The ability to derive both inherited and acquired genetic alterations in a single step over 6800 genes with the present procedure, using the Affymetrix array as an example, is described below.

Inherited single nucleotide polymorphisms (SNPs) are estimated to be present in the two alleles of each gene with a frequency of ~1:1000 bases. When an SNP in the coding sequence causes a debilitating change in the protein, heterozygous mutations arise which could result to early onset of cancer (e.g. the Li-Fraumeni syndrome). When cDNA from normal cells is melted and self-hybridized, mismatches will occur at positions of heterozygocities and SNPs, whenever both alleles are expressed, which will be detectable by the present technology (A.L.B.U.M.S) and would display positive on the DNA arrays. Because SNPs among alleles occur at a high frequency (~1:1000 bp) it is possible that within every single gene (average~2,000 bp) there is one or more SNPs. Therefore, if both paternal and maternal alleles are transcribed, self-hybridizing cDNA from whole genes would be expected to result in one or more mismatches per gene, as a result of allelic cross-hybridization. All array elements would then display positive, resulting to trivial information. By digesting the cDNA to ~100–200 bp pieces prior to ALBUMS genotypic selection (as described in example 3) the problem is avoided: Most fragments are likely to contain none, or occasionally one inherited SNP. ALBUMS will select mismatch-containing fragments, and array elements that score positive will be only those capturing a 100–200-mer gene fragment with an SNP.

Acquired mutations can be detected by following the same strategy, and by using cancer samples from the same individual as the normal sample. Again, by self-hybridizing cDNA from cancer samples and fragmenting to 100–200-mers, it is likely that most fragments will contain none, or occasionally one inherited SNP, or very occasionally one acquired mutation. Array elements that score positive will be those corresponding to genes that contain either inherited or acquired mutations, but rarely both.

Figure 12:
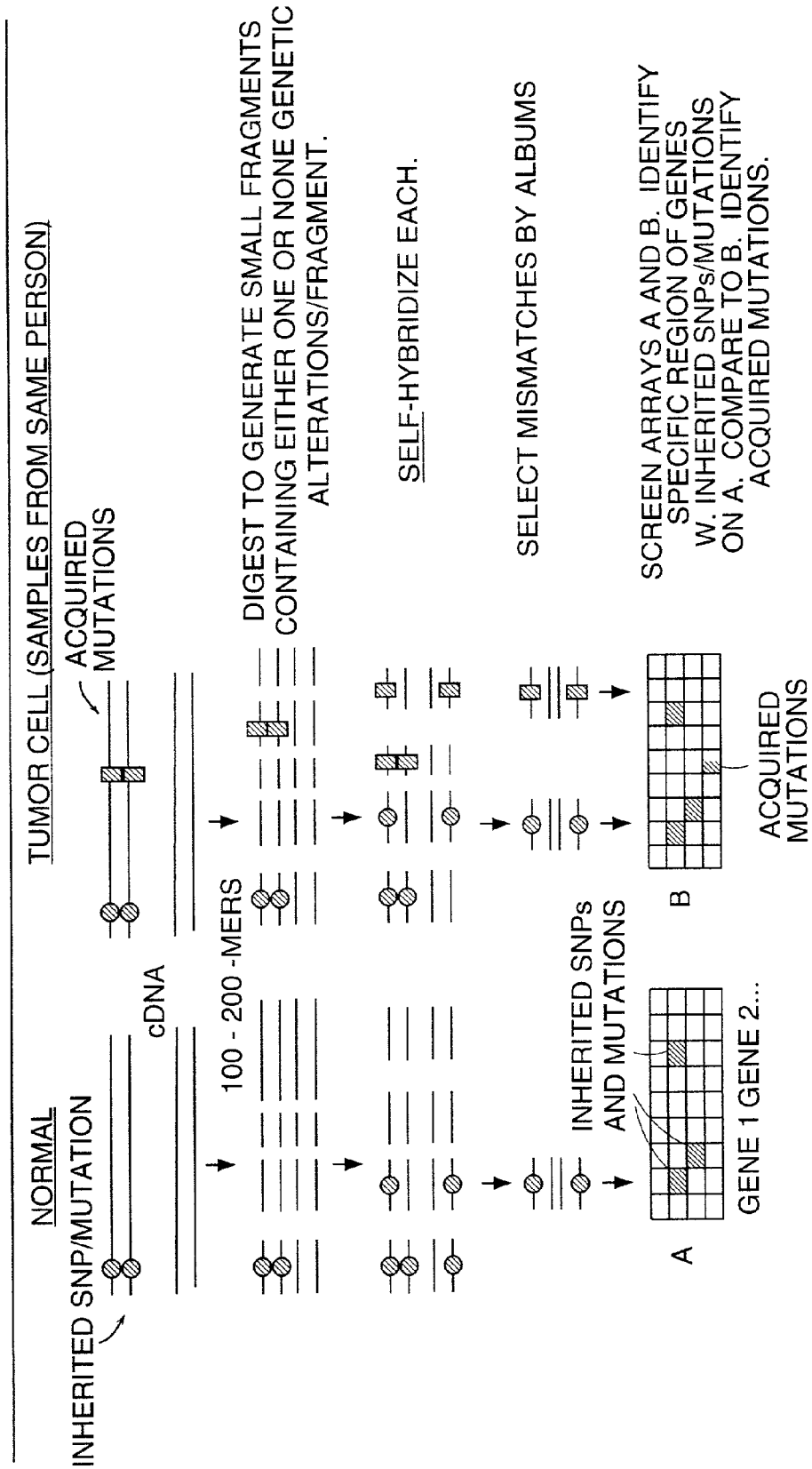
FIG. 12 is a schematic showing how the method of mismatch identification can be used with a DNA chip to detect inherited and acquired predisposition to cancer (see text).

An example of using the high resolution Affymetrix array (described earlier) to detect genetic alterations in parallel normal and cancer samples is displayed in FIG. 12. cDNA from normal tissue is melted and self-hybridized to generate mismatches (FIG. 12), then digested with appropriate enzymes to generate 100–200-mers and add primers; then the present technology, (ALBUMS), utilizing one of the probes (FARP, AED or BARP) selects the mismatches, PCR amplifies them and these are applied on the Affymetrix array: The mutation-containing 200-mers isolated via ALBUMS will cause certain 25-mer array elements to display positive, thereby identifying both the gene and the approximate (±100–200 bp) location of an inherited polymorphism among the two alleles.

Next, cDNA from the cancer sample is melted, self-hybridized and processed similarly. Acquired mutations will show up as positive array elements that are negative on the normal tissue array. Acquired mutations scored on the same gene as an inherited mutation provide candidate genes to be examined for loss of heterozygocity, using existing methodologies. Finally, cDNA from cancerous cells will be cross-hybridized to cDNA from normal cells and the procedure will be repeated (not illustrated in FIG. 12). This will detect acquired mutations in those genes that express a single allele in their mRNA, which would not be detected by self-hybridization alone.

The use of the Clontech array will provide similar information to the Affymetrix array. However, this array would be used with fewer genes and with smaller 'resolution', since the array elements contain 500 bases-long cDNA and it is possible that certain elements will capture both inherited SNPs and acquired mutations, thereby providing unclear information. On the other hand these arrays are simpler to use and do not require the fluorescent laser scanner, hence they are currently more accessible to users.

EXAMPLE 7

Use of Microbead Mutation Scanning Array

ALBUMS was utilized as described above to isolate mutation-containing DNA fragments out of a mixture of diverse DNA fragments. In this system, we inserted a mutation in the p53 gene and we then used ALBUMS to select the mutation-containing fragment. Microbeads coated with oligonucleotides having a sequence complementary to the known, mutation-containing sequence, were then constructed and used to demonstrate detection. The methods and results are presented below:

a. Conjugation of Oligonucleotides onto Caboxylated Microspheres
1. Vortex carboxylated microspheres (from Molecular Probes) stock.
2. 5,000,000 microspheres are dispensed into a 1.5 ml microcentrifuge tube.
3. Disperse the microspheres by sonication for 30 seconds.
4. Centrifuge the microspheres at 8000 g for 1 minute.
5. Remove the supernatant.
6. Add 50 ul of 0.1 M MES (2-(N-Morpholino) ethanesulfonic acid) (pH 4.5). Vortex.
7. Add 1 nmole of oligonucleotide (5'-amino-unilinker-25 mer-3') to microspheres. Vortex briefly.
8. Immediately before use, add 1 ml sterile water to 10 mg of EDC (1-ethyl-3-(3-dimethyaminopropyl) carbodiimide-HCl). Vortex until dissolved.
9. Add 2.5 ul of the fresh EDC solution to the microspheres. Vortex immediately.
10. Incubate for 30 minutes at room temperature.
11. Repeat steps 8–10 with fresh EDC.
12. Add 1.0 ml of 0.02% Tween 20. Vortex.
13. Centrifuge microspheres at 8000 g for 1 minute.
14. Remove the supernatant.
15. Add 1.0 ml of 0.1% SDS. Vortex.
16. Centrifuge microspheres at 8000 g for 1 minute.
17. Remove the supernatant.
18. Resuspend the microspheres in 100 ul of 0.1 M MES (pH 4.5).
19. Store the preparation at 4° C.

b. Hybridization and capturing of ALBUMS-derived PCR fragments onto microspheres.
DNA Hybridization
1. Add DNA 17 Tl of diluent (TE, etc.) to the control tube.
2. Add DNA (1, 5, 10, 25 ng) in 17 Tl of volume to the sample tubes.
3. Incubate all tubes at the 96° C. heatblock for 10 minutes.
4. Vortex and sonicate oligo LGA-conjugated microspheres.
5. Dilute microspheres in 1.5×TMAC (Tetramethylammonium chloride) to a concentration of 10,000 microspheres per 33 ul of 1.5×TMAC hybridization buffer.
6. Place microspheres/1.5×TMAC mixture at hybridization temperature (50° C.)
7. With the tubes still in the 96° C. heatblock, add 33 Tl of microspheres/1.5×TMAC mixture with hybridization temperature to the first tube.
8. Immediaterly close, remove and vortex the first tube.
9. Place the first tube at hybridization temperature.
10. Repeat steps 7–9 for all remaining tubes.
11. Incubate all tubes at hybridization temperature for 10 minutes.
12. Wash microspheres with PBS (pH 7.4).
13. Centrifuge tubes at 8000 g for 5 minutes. Remove supernatant.
14. Add 50 Tl of PBS (pH 7.4) to the tubes.
15. Dilute streptavidin-alexa-488 to 10 Tg/ml in PBS (pH 7.4)
16. Add 12 ul of streptavidin-alexa-488 to the tubes.
17. Incubate tubes at room temperature for 15 minute.
18. Analyze samples with flow cytometer.

c. Measurement of microsphere-Bound DNA Sequences on a Flow Cytometer.

Figure 14:
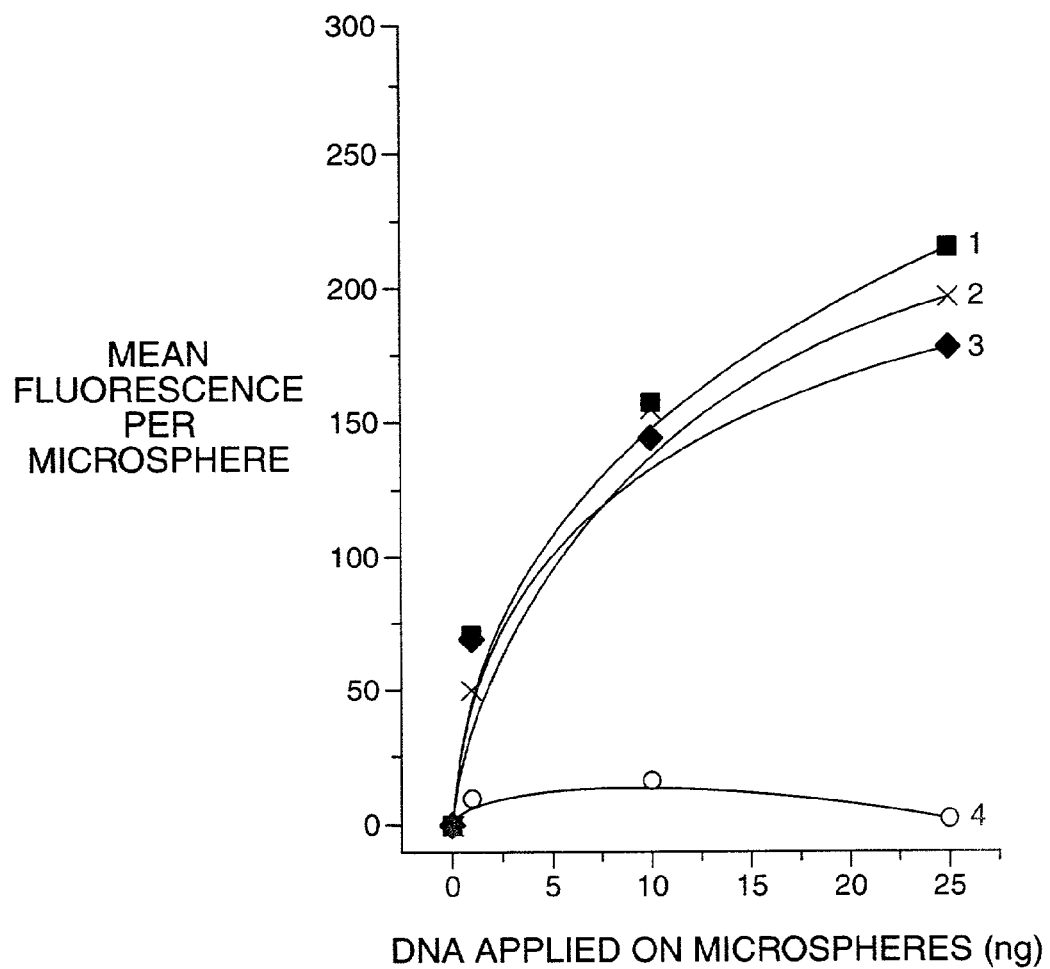
FIG. 14 demonstrates the results of four different hybridization experiments.

Following hybridization of fluorescently-tagged ALBUMS-derived DNA sequences on microbeads, the sample was processed for flow cytometry, to identify the presence of sequences complementary to the sequences conjugated to the microbeads. FIG. 14 demonstrates the results of 4 different hybridization experiments, as a function of the amount of DNA applied for hybridization to the microspheres: Curves 1–3 represent ALBUMS-derived DNA fragments that are 236, 86 and 57 base pair long, and all contain a sequence complementary to the microsphere-sequence. Curve 4 represents the hybridization of irrelevant (non-complementary) DNA sequences to the microspheres. A clear signal is observed only when the hybridized DNA sequences are complementary to the microbead-bound sequence.

Figure 15:
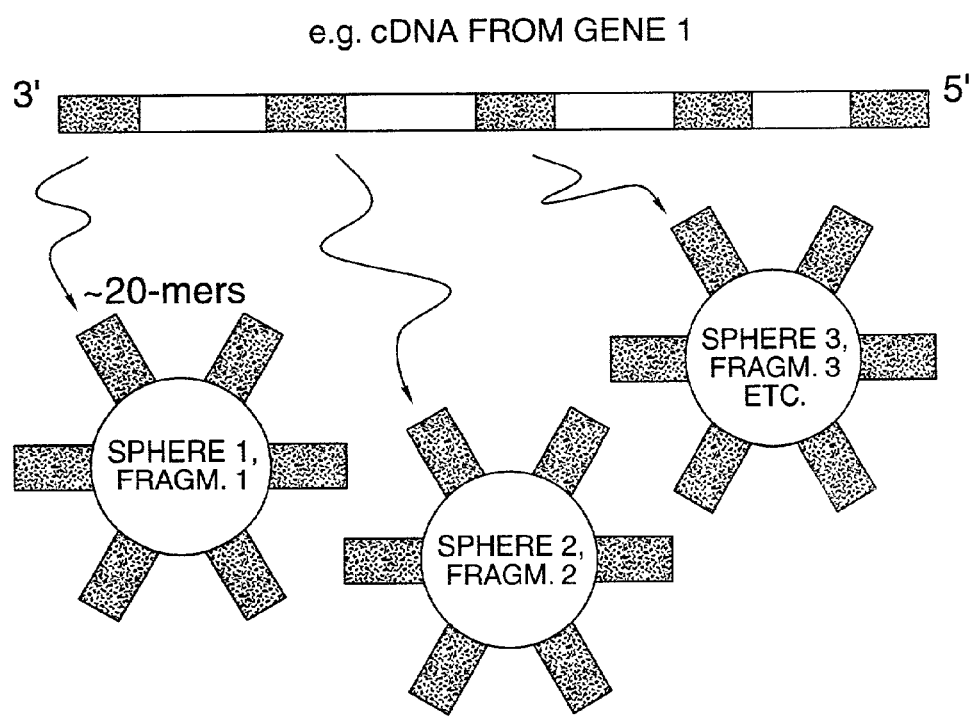
FIG. 15 shows how a microbead (miscosphere)-based mutation scanning array is constructed.

Therefore we have demonstrated the ability of the system to specifically detect the presence or absence of certain sequences in the sample. In the simplified example shown above, the microspheres were not 'optically encoded', and only one set of microspheres was used. To construct a full Mutation Scanning Array, several sets of optically encoded microspheres can be used, each set containing a different sequence. By hybridizing the ALBUMS-derived DNA fragments to a mixture of different microspheres, readings from different micospheres can be simultaneously obtained over hundreds or thousands of sequences, via flow-cytometry. An illustration of how a microsphere-based Mutation Scanning Array is constructed, is presented in FIG. 15.

All references discussed herein are incorporated herein by reference.

What is claimed is:

1. A method of using a mutation scanning array to identify mutation in a target DNA sequence, wherein said mutation scanning array comprises a plurality of elements, wherein the elements contain immobilized oligonucleotides 8–50 bases long, that collectively span at least 5 different genes, wherein said method comprises:
  (a) hybridizing the target DNA sequence with a control DNA sequence wherein said control DNA sequence is the wild-type DNA sequence corresponding to the target DNA sequence to create a duplex, and wherein said target DNA comprises a pool of nucleotide segments that collectively span at least 5 different genes;
  (b) digesting the duplex to fragments of 50–300 base pairs, with restriction enzymes that allow generic addition of PCR primers;
  (c) adding PCR primers to the duplex
  (d) treating the duplex to remove any spontaneous aldehydes;
  (e) reacting the duplex with a repair glycosylase to convert any mismatched sites in the duplex to reactive sites containing an aldehyde-containing abasic site;
  (f) reacting the duplex with a compound of the formula X—Z—Y, wherein X is a detectable moiety, Y is NHNH2, O—NH2 or NH2, and Z is a hydrocarbon, alkyhydroxy, alkylethoxy, alkylester, alkylether, alkylamide or alkylamine, wherein Z may be substituted or unsubstituted; or where Z may contain a cleavable group; for a sufficient time and under conditions to covalently bind to the reactive sites;
  (g) detecting the bound compound to identify sites of mismatches;
  (h) isolating the DNA that contains mismatches from DNA without mismatches;
  (i) PCR-amplifying the mismatch-containing DNA
  (j) applying the mismatch-containing DNA on the Mutation Scanning Array, to determine the genomic position(s) where mismatches occur; and
  k) determining whether the mismatch is a mutation or polymorphism.

2. The method of claim 1, where the detectable moiety is selected from the group consisting of $NH_2$, SH, $NHNH_2$, a fluorescein derivative, a hydroxycoumarin derivative, a rhodamine derivative, a BODIPY derivative, a digoxigenin derivative and a biotin derivative.

3. The method of claim 1, wherein the target DNA sequence comprises at least 5 genes, wherein each individual gene is represented by a set of oligonucleotides which collectively spans that individual whole gene from the 5' to 3' end.

4. The method of claim 1, wherein the segments tagged with the detectable moiety are amplified before being used on the mutation scanning array.

5. The method of claim 1, wherein each gene on the mutation scanning array is represented by array elements; each element containing immobilized oligonucleotides that sample in 25–300 bases for the whole 3' to 5' mRNA sequence of each represented gene.

6. The method of claim 1, wherein each of the array genes is represented by the coding portion of the gene.

7. The method of claim 1, wherein each of the array genes is represented by both the coding and non-coding genomic portions of a gene.

8. The method of claim 1, wherein said at least 5 different array genes are collectively known to predispose an individual to a particular disease.

9. The method of claim 8, where the disease is a particular kind of cancer.

10. The method of claim 8, where the disease is a cardiovascular abnormality, or a neurodegenerative disorder, or diabetes.

11. The method of claim 9, where said array genes are all known tumor suppressor genes or oncogenes.

12. The method of claim 1, where said array genes are genes known to be overexpressed in a malignant cell, wherein overexpression is determined by comparison to the gene's expression in a corresponding non-malignant cell.

* * * * *